(12) United States Patent
Rahman

(10) Patent No.: US 9,512,486 B2
(45) Date of Patent: Dec. 6, 2016

(54) MATERIALS, METHODS, AND SYSTEMS FOR TREATING CANCER

(71) Applicant: The Institute of Cancer Research: Royal Cancer Hospital, London (GB)

(72) Inventor: Sabera Nazneen Rahman, London (GB)

(73) Assignee: The Institute of Cancer Research: Royal Cancer Hospital, London (GB)

(*) Notice: Subject to any disclaimer, the term of this patent is extended or adjusted under 35 U.S.C. 154(b) by 9 days.

(21) Appl. No.: 13/960,537

(22) Filed: Aug. 6, 2013

(65) Prior Publication Data

US 2014/0045853 A1    Feb. 13, 2014

Related U.S. Application Data

(60) Provisional application No. 61/680,016, filed on Aug. 6, 2012.

(51) Int. Cl.
*C12Q 1/68* (2006.01)
*A61K 31/502* (2006.01)

(52) U.S. Cl.
CPC ........... *C12Q 1/6886* (2013.01); *A61K 31/502* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 7,097,977 B1 * | 8/2006 | Takeda et al. | 435/6.13 |
| 2008/0009419 A1 * | 1/2008 | Ralph et al. | 506/7 |
| 2009/0028861 A1 * | 1/2009 | Takagi et al. | 424/138.1 |
| 2009/0029375 A1 * | 1/2009 | Jupe et al. | 435/6 |
| 2011/0053911 A1 * | 3/2011 | Ingenito et al. | 514/212.02 |
| 2012/0135983 A1 * | 5/2012 | Ashworth et al. | 514/218 |
| 2014/0050723 A1 * | 2/2014 | Hansen et al. | 424/133.1 |

FOREIGN PATENT DOCUMENTS

| WO | WO 2011058367 A2 * | 5/2011 |
|---|---|---|
| WO | WO 2013184905 A1 * | 12/2013 |

OTHER PUBLICATIONS

Mayo Clinic (Alternative cancer treatments: 10 options to consider, accessed Apr. 23, 2015, available at http://www.mayoclinic.org/diseases-conditions/cancer/in-depth/cancer-treatment/art-20047246).*
Kinde et al. (Detection and quantification of rare mutations with massively parallel sequencing, Proc Natl Acad Sci U S A. Jun. 7, 2011;108(23):9530-5. Epub May 17, 2011).*
SNPedia (Ovarian cancer, Jun. 23, 2011, available at http://www.snpedia.com/index.php/Ovarian_cancer).*
ENSEMBL (Gene: RAD51D ENSG00000185379, attached, accessed Apr. 23, 2015).*
NM_002878 BLAST, attached, performed Apr. 23, 2015.*
Loveday et al. (Germline mutations in RAD51D confer susceptibility to ovarian cancer, Nature Genetics 43, 879-882 (2011), Published online Aug. 7, 2011).*
Osher et al. (Mutation analysis of RAD51D in non-BRCA1/2 ovarian and breast cancer families, Br J Cancer. Apr. 10, 2012;106(8):1460-3. Epub Mar. 13, 2012).*
Nadkarni et al. (Functional analysis of the Rad51d (E233G) breast cancer associated polymorphism and a pharmacogenetic evaluation of RAD51D status, (Jul. 29, 2008), The University of Toledo, The University of Toledo Digital Repository, Theses and Dissertations, Paper 1219).*
Banerjee et al. (Making the best of PARP inhibitors in ovarian cancer, Nat Rev Clin Oncol. Sep. 2010;7(9):508-19. Epub Aug. 10, 2010).*
Rozen et al. (Primer3 on the WWW for General Users and for Biologist Programmers, in Methods in Molecular Biology, vol. 132: Bioinformatics Methods and Protocols, 2000).*
Buck et al. ("Design Strategies and Performance of Custom DNA Sequencing Primers" Biotechniques. 1999. 27(3): pp. 528-536).*
Lowe et al. (Nucleic Acids Research, vol. 18, No. 7, p. 1757-1761, 1990).*
NCBI Accession No. NM_002878 (Jul. 6, 2011 revision).*
Seq ID No. 3 BLAST, attached, performed Apr. 23, 2015.*
Seq ID No. 24 BLAST, attached, performed Apr. 23, 2015.*
Pelttari et al. (A Finnish founder mutation in RAD51D: analysis in breast, ovarian, prostate, and colorectal cancer, J Med Genet. Jul. 2012;49(7):429-32. Epub May 31, 2012).*
Smith et al. (High sensitivity for BRCA1I2 mutations in breast/ovarian kindreds: are there still other breast/ovary genes to be discovered?, Breast Cancer Res Treat. Jul. 2012;134(2):895-7. Epub Jul. 3, 2012).*
Rodriguez-Lopez et al. (The Variant E233G of the RAD51D Gene Could Be a Low-Penetrance Allele in High-Risk Breast Cancer Families Without BRCA1/2 Mutations, Int J Cancer. Jul. 20, 2004;110(6):845-9).*
Smiraldo et al. (Extensive Chromosomal Instability in Rad51d-Deficient Mouse Cells, Cancer Res. Mar. 15, 2005;65(6):2089-96).*
Michiels et al. (Genetic polymorphisms in 85 DNA repair genes and bladder cancer risk, Carcinogenesis. May 2009;30(5):763-8. Epub Feb. 23, 2009).*
Jara et al. (Variants in DNA double-strand break repair genes and risk of familial breast cancer in a South American population, Breast Cancer Res Treat. Aug. 2010;122(3):813-22. Epub Jan. 7, 2010).*

* cited by examiner

*Primary Examiner* — Aaron Priest
(74) *Attorney, Agent, or Firm* — Faegre Baker Daniels LLP

(57) ABSTRACT

Aspects of the invention relate to methods of treatment, and to kits and systems for the same including materials for determining that an individual is susceptible to cancer and if warranted treating the patient of cancer or initiating a monitoring strategy and/or taking a preventive action. Therapeutic and preventive interventions include, treating the patient with a PARR inhibitors and/or laprascopic oophorectomy. The invention also relates to systems and methods of genotyping an individual, and to methods of identifying a patent with a higher than normal likelihood of developing cancer and/or genetically related individuals or groups at heighten risk for developing cancer, particularly ovarian cancer.

3 Claims, 14 Drawing Sheets

MATERIALS, METHODS, AND SYSTEMS FOR TREATING CANCER

PRIORITY CLAIM

This application claims priority to U.S. provisional patent application No. 61/680,016 filed on Aug. 6, 2012, which is incorporated by reference in its entirety.

FIELD OF THE INVENTION

Aspects of the invention relate to methods of treatment, and to kits and systems for the same including materials for determining that an individual is susceptible to developing cancer and if warranted treating the patient for cancer or initiating a monitoring strategy and/or taking a preventive action. The invention also relates to methods of genotyping an individual, and to methods of identifying a patent with a higher than normal likelihood of developing cancer and/or genetically related individuals or groups at heighten risk for developing cancer, particularly ovarian cancer.

BACKGROUND AND SUMMARY

Until recently hereditary ovarian carcinoma has been attributed almost entirely to mutations in the BRCA1 and BRCA2 genes, with a much smaller contribution from mutations in DNA mismatch repair genes. However, there now is growing acceptance that rare mutations may substantially impact ovarian cancer risk, and account for a significant proportion of the 'missing heritability' of ovarian cancer.

While mutations in genes other than BRCA1 and BRCA2 are each individually rare, together they make up a significant proportion of cases. With at least 16 genes implicated in hereditary ovarian cancer to date, comprehensive testing for ovarian cancer risk is likely to utilise assessment of many genes. The falling cost of genomic sequencing and new advances in genomic technologies increase the feasibility of comprehensive evaluation of multiple genes simultaneously at low cost. Improved recognition of inherited risk will identify individuals who are candidates for targeted prevention.

Homologous recombination (HR) is a mechanism for repairing stalled replication forks, DNA interstrand cross-links and double-strand breaks. Constitutional inactivating mutations in several genes that encode proteins crucial for DNA repair by HR have been shown to predispose to cancer. In particular, there is a strong association with female cancers and mutations in genes such as BRCA1, BRCA2, ATM, BRIP1, CHEK2, PALB2, RAD50 and RAD51C have been shown to confer susceptibility to breast and/or ovarian cancer. Indeed, the analysis of families with breast and ovarian cancer was crucial to the mapping of the BRCA1 gene. For many years, it was widely believed that the genetic contribution to families with breast and ovarian cancer was largely attributable to mutations in BRCA1 and BRCA2. However, RAD51C mutations have recently been identified in breast-ovarian cancer families. This suggested that analysis of such families may still have utility in cancer predisposition gene discovery.

In eukaryotic cells, DNA repair by HR involves several proteins of which a central player is the DNA recombinase RAD51, the ortholog of bacterial RecA. RAD51 forms helical filaments on DNA and catalyzes DNA strand invasion and exchange. Multiple other proteins are involved in these processes including five RAD51 paralogs: RAD51B, RAD51C, RAD51D, XRCC2 and XRCC3.

In a first aspect the invention provides a method of determining that an individual is susceptible to cancer, the method comprising assaying a sample comprising a RAD51D-encoding nucleic acid molecule, or a complement thereof, from a human subject for the presence of an inactivating mutation in said nucleic acid, wherein the presence of an inactivating mutation in the nucleic acid indicates that the individual is susceptible to cancer.

In a second aspect, the invention provides a method of predicting a likelihood of a human subject developing cancer, the method comprising assaying a sample comprising a RAD51D-encoding nucleic acid molecule, or a complement thereof, from the human subject for the presence of an inactivating mutation in said nucleic acid, wherein the presence of an inactivating mutation in said nucleic acid indicates that the individual has an increased likelihood of developing cancer.

In a third aspect, the invention provides a method of treatment, the method comprising determining that a patient has cancer, assaying a sample comprising a RAD51D-encoding nucleic acid molecule, or a complement thereof, from the patient for the presence of a mutation in said nucleic acid, and, where a mutation is found in said nucleic acid, treating the patient using a DNA damaging agent or Topoisomerase I (TOPO I) inhibitor.

In a fourth aspect, the invention provides a method of treatment, the method comprising determining that a patient has cancer, assaying a sample comprising a RAD51D-encoding nucleic acid molecule, or a complement thereof, from the patient for the presence of an inactivating mutation in said nucleic acid, and, where an inactivating mutation is found in said nucleic acid, treating the patient using a poly (ADP-ribose) polymerase (PARP) inhibitor.

In a fifth aspect, the invention provides a method of genotyping a human subject, the method comprising assaying a sample comprising a RAD51D-encoding nucleic acid molecule, or a complement thereof, from a human subject for the presence of an inactivating mutation in said nucleic acid. In a suitable embodiment the inactivating mutation may be selected from the group consisting of: c.363delA; c.803G>A; c.480+1G>A; c.345G>C; c.556C>T; c.757C>T; c.270-271dupTA; and optionally c.748delC.

In a sixth aspect, the invention also provides a kit comprising oligonucleotides capable of amplifying an inactivating mutation in a RAD51D-encoding nucleic acid molecule, or a complement thereof, from a human subject. A kit in accordance with this fifth aspect of the invention may be of use in the various methods of the invention.

In a seventh aspect, the invention provides a system for determining a predisposition to cancer in a subject, comprising: (i) a sample analyzer for determining the RAD51D gene status in a sample from the subject, wherein the sample analyzer contains the sample, DNA extracted from the sample, RNA expressed from a RAD51D gene in the sample, complementary DNA synthesized from the RNA, DNA amplified from such extracted DNA and/or complementary DNA; (ii) a computer program for receiving the RAD51D gene status data for the sample; and (ii) a computer program for comparing the RAD51D gene status data for the sample to the reference RAD51D gene status associated with a predetermined degree of predisposition to cancer.

An eighth aspect of the invention is a diagnostic system, comprising: a polynucleotide sequence, the sequence including; a sample intake suitable for the intake of tissue, blood, or cells; a first reservoir in fluid contact the sample intake, the first reservoir includes a buffer and at least one pair of complementary polynucleotide primers that have at least 90 percent identity to at least two polynucleotides selected from the group consisting of SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17, SEQ ID NO.: 18, SEQ ID NO.: 19, SEQ ID NO.: 20, SEQ ID NO.: 21, SEQ ID NO.: 22, SEQ ID NO.: 23, and SEQ ID NO.: 24; a second reservoir in fluid contact with the sample intake, the second reservoir includes a second buffer and a nucleic acid polymerase; a mixing chamber, in fluid contact with the sample intake, the first reservoir, the second reservoir; and the nucleic acid polymerase, where the mixing chamber mixes and incubates a mixture of the sample, the polynucleotide primers; and the nucleic acid polymerase, until the mixture amplifies a polynucleotide having 5' and 3' ends comprising said two polynucleotide primers to produce amplified polynucleotide; a mechanism for determining a sequence of nucleotide bases in the amplified polynucleotide, the mechanism is in fluid contact with the mixing chamber; a controller, the controller includes a compilation of the sequence of the amplified polynucleotide; a register of RAD51D (SEQ ID NO.: 1) truncation mutations, including at least one RAD51D truncation mutation selected from the group consisting of: c.363delA; c.803G>A; c.480+1G>A; c.345G>C; c.556C>T; c.757C>T; c.270-271dupTA; and c.748delC; a processor, the processor matches the sequence of the amplified polynucleotide to the truncation mutation in the register; and produces an output; the output includes: the sequence of the amplified polynucleotide; and a match between the sequence and any mutation in the register if the match exists.

SEQUENCE LISTING

SEQ ID NO: 1

```
   1 CTGGAACCCGGAAGCGGCAGCGCGGCGCGACCCGGCGGGCGGGCTCTGGGCGCGGAATC
  61 CCGGCGGATCCCGGGCGGGCGGATGACCCCCAGCCCTACCCTTGGTGCCGCCTCCTCCTC
 121 TCTCCTTTCTCCTCGGCAGCCAGCGCGCCTGTGTCCTCTCTAGGAAGGGGTAGGGGAGG
 181 GGCGTCTGGAGAGGACCCCCGCGAATGCCCACGTGACGTGCAGTCCCCCTGGGGCTGTT
 241 CCGGCCTGCGGGGAACATGGGCGTGCTCAGGGTCGGACTGTGCCCTGGCCTTACCGAGGA
 301 GATGATCCAGCTTCTCAGGAGCCACAGGATCAAGACAGTGGTGGACCTGGTTTCTGCAGA
 361 CCTGGAAGAGGTAGCTCAGAAATGTGGCTTGTCTTACAAGGCCCTGGTTGCCCTGAGGCG
 421 GGTGCTGCTGGCTCAGTTCTCGGCTTTCCCCGTGAATGGCGCTGATCTCTACGAGGAACT
 481 GAAGACCTCCACTGCCATCCTGTCCACTGGCATTGGCAGTCTTGATAAACTGCTTGATGC
 541 TGGTCTCTATACTGGAGAAGTGACTGAAATTGTAGGAGGCCCAGGTAGCGGCAAAACTCA
 601 GGTATGTCTCTGTATGGCAGCAAATGTGGCCCATGGCCTGCAGCAAAACGTCCTATATGT
 661 AGATTCCAATGGAGGGCTGACAGCTTCCCGCCTCCTCCAGCTGCTTCAGGCTAAAACCCA
 721 GGATGAGGAGGAACAGGCAGAAGCTCTCCGGAGGATCCAGGTGGTGCATGCATTTGACAT
 781 CTTCCAGATGCTGGATGTGCTGCAGGAGCTCCGAGGCACTGTGGCCCAGCAGGTGACTGG
 841 TTCTTCAGGAACTGTGAAGGTGGTGGTTGTGGACTCGGTCACTGCGGTGGTTTCCCCACT
 901 TCTGGGAGGTCAGCAGAGGGAAGGCTTGGCCTTGATGATGCAGCTGGCCGGAGAGCTGAA
 961 GACCCTGGCCCGGGACCTTGGCATGGCAGTGGTGGTGACCAACCACATAACTCGAGACAG
1021 GGACAGCGGGAGGCTCAAACCTGCCCTGGACGGTCCTGGAGCTTTGTGCCCAGCACTCG
1081 GATTCTCCTGGACACCATCGAGGGAGCAGGAGCATCAGGCGGCCGGCGCATGGCGTGTCT
1141 GGCCAAATCTTCCCGACAGCCAACAGGTTTCCAGGAGATGGTAGACATTGGGACCTGGGG
```

```
1201 GACCTCAGAGCAGAGTGCCACATTACAGGGTGATCAGACATGACCTGTGCTGTTGTTTGG

1261 GAAACAGGGAAGCATTGGGGACCCCTCCCAACTTTTCTTCCCAGTAACGCCTGCTGTTTA

1321 CTGCCACCTGGCACTGGTGACTACAGACGTTCTCAGGCTGGCCAGAAGAGACATCTTGGG

1381 TTCCTTGGCCTCACTCTCTGTAAGCATATAAACCACAGGCGAAAGAGGATGCTGCATTGC

1441 GAGGACCCAGAAATTCATACTGGTGCCACGTTTCCTTCCCTTATTTCTAACGTGTATGTT

1501 TCTGGTGGAAACCAAGTTCACCCTGGCTGGGAGCATCTCTGATGAGGCATGCTGGCGACT

1561 GGATGGATAATCCTGTGCATCACCATTGTGTCCTGTGCTCCCTCCTAGCGCAGTGGCCAA

1621 GCCGGGAAAGCCTCTAACTTGCCTTTGCTGCTGCTGCCTTTTTTTTCTTTTGTCTCTGCC

1681 TTTCCATTTGTTAGATGGGGGCCCACTCTTCCTTAGCTCTGTCTCTGAGTTACTGGGTGG

1741 AAATAAGCTTATAAATGAAATACTCTTCCTTCATCTCTGTTTTGCTCTTAAAAATATAAAA

1801 AGGCAATTCCCCGAGCCCTAGAGCCACCTGATTTCCCCTTAGAAGGCTGTTTTTCAGTTT

1861 CCCCCAGTGAGGCCCAAAGAACAGTTTATTCCTCCTTTCCTCTTGCTGATTTGGTTTCAG

1921 ACCTGCCTGCATCACCATGACTAGGTGAGAACGTGTGGGCTCGCTGCAGTTCCAGGGATA

1981 TAATTTAACAGAAAGGGAGGGTATGACCCTGCTCCTGGTGAATCCAGCCACTCATTTAATA

2041 TGCATGGTGCCCTGTGGGGCCCCTCCACAGTACAGCATAACCAGAGGTGCTGAACCATGG

2101 CCTTGCCCATAAACAGACAGAGGAGAATTTGCACAGTAAATAGAGCCAGCTGGGAAAATT

2161 GATGCTGACGTAAATAATACATGGCAAATCTAGTCCTTTATGCAGAAATTCATTGCTGGT

2221 GGCTCCAAGATGCAATATAATTACACCCTCTCTTCCTGCCAGCTGTACCACAGCTAGTGCC

2281 CTAGTGTATGAAATAATCCCTCTGTCTTTCACCAGCACTGTGGCCATCCGTCTGAGAGCC

2401 ATGACCCTGGCTGGGAGGGGACGAAGACACCAGGGAATGGAAAATAAAAGGAAAAGTACA

2401 GAA; source Homo sapiens.
                                                        SEQ ID NO.: 2
MGVLRVGLCPGLTEEMIQLLRSHRIKTVVDLVSADLEEVAQKCGLSYKALVALRRVLLAQ

FSAFPVNGADLYEELKTSTAILSTGIGSLDKLLDAGLYTGEVTEIVGGPGSGKTQVCLCM

AANVAHGLQQNVLYVDSNGGLTASRLLQLLQAKTQDEEEQAEALRRIQVVHAFDIFQMLD

VLQELRGTVAQQVTGSSGTVKVVVVDSVTAVVSPLLGGQQREGLALMMQLARELKTLARD

LGMAVVTNHITRDRDSGRLKPALGRSWSFVPSTRILLDTIEGAGASGGRRMACLAKSSR

QPTGFQEMVDIGTWGTSEQSATLQGDQT; source Homo sapiens.

SEQ ID NO.: 3  GCCTCCTCCTCTCTCCTTTC, 5'-3', synthetic primer.
SEQ ID NO.: 4  CACCCTTCCTGAGCCTCTC, 3'-5', synthetic primer.
SEQ ID NO.: 5  GGGTAGAATTGACACCCCATT, 5'-3', synthetic primer.
SEQ ID NO.: 6  TGACTTCTGACTCCAAGTGACC, 3'-5', synthetic primer.
SEQ ID NO.: 7  AAAGGGAGCAGAGGGTTCTC, 5'-3', synthetic primer.
SEQ ID NO.: 8  ATGTCCTGACCCCTTTCCTT, 3'-5', synthetic primer.
SEQ ID NO.: 9  TGGCCAGTGATGTTCAAAGA, 5'-3', synthetic primer.
SEQ ID NO.: 10 CCCATTAGTACGCTGAAGCTC, 3'-5', synthetic primer.
SEQ ID NO.: 11 GGACTCAGCCCATTTGTGTT, 5'-3', synthetic primer.
SEQ ID NO.: 12 AGCAAGTTTGAAGGCAAGGA, 3'-5', synthetic primer.
```

-continued

```
SEQ ID NO.: 13 CTGAGTCCTTGCATCCAGGT, 5'-3', synthetic primer.
SEQ ID NO.: 14 ATTGCACATCTGCATTTCCA, 3'-5', synthetic primer.
SEQ ID NO.: 15 CTTGCTGTATTTGGGATGGG, 5'-3', synthetic primer.
SEQ ID NO.: 16 TTTGGGGTTCAGAAGCTGAC, 3'-5', synthetic primer.
SEQ ID NO.: 17 CTCTCCGTAAAATGAAGCGG, 5'-3', synthetic primer.
SEQ ID NO.: 18 TAAACAGCAGGCGTTACTGG, 3-5', synthetic primer.
SEQ ID NO.: 19 CAGAACCAGTGCTTGAAAGAAA, 5'-3', synthetic primer.
SEQ ID NO.: 20 GGCCTCACATGTACCTGAGTT, 3'-5', synthetic primer.
SEQ ID NO.: 21 GAATCTGGGCAAGGTTTGGT, 5'-3', synthetic primer.
SEQ ID NO.: 22 TGGGTTTTAGCCTGAAGCAG, 3'-5', synthetic primer.
SEQ ID NO.: 23 AGGCCTCTGTTTTCCTCTCC, 5'-3', synthetic primer.
SEQ ID NO.: 24 CGATGGTGTCCAGGAGAATC, 3'-5', synthetic primer.
```

BRIEF DESCRIPTION OF THE FIGURES

FIG. 3.B. Graphic illustration of the effect of Olaparib concentration on Surviving Fraction, measured in siRAD51D OLIGO1, siRAD51D OLIGO 2and siRAD51D POOL.
FIG. 3.C. Graphic illustration of the effect of Olaparib concentration on Surviving Fraction, measured in RAD51D Wild Type and RAD51D Mutant.

DETAILED DESCRIPTION

Figure 1A:
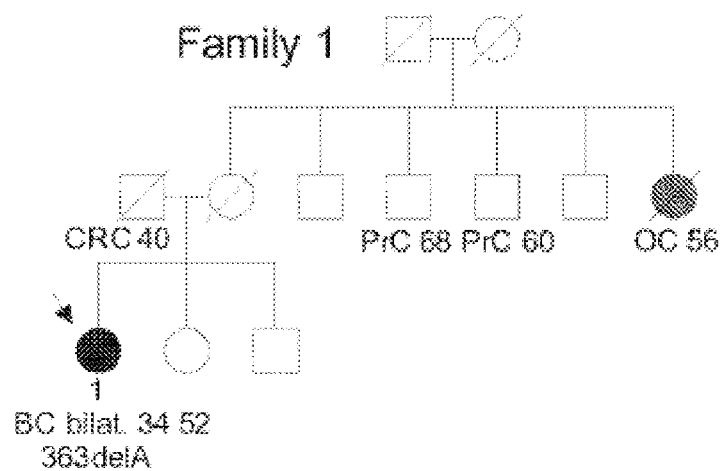
FIG. 1A. Abridged pedigree of a family with RAD51D.
Figure 1B:
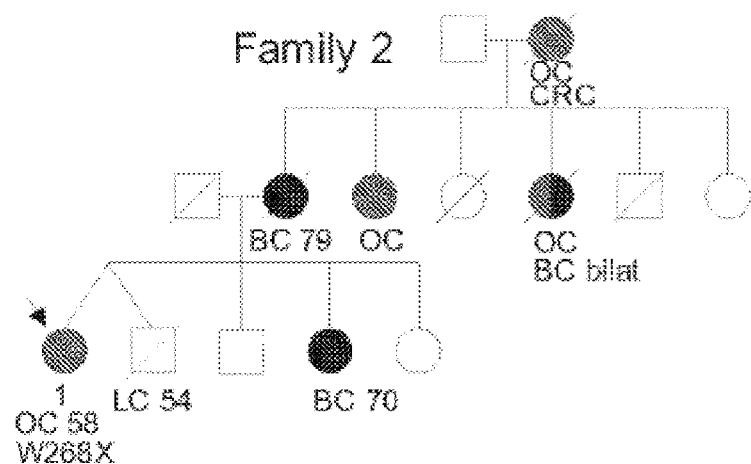
FIG. 1B. Abridged pedigree of a family with RAD51D.
Figure 1C:
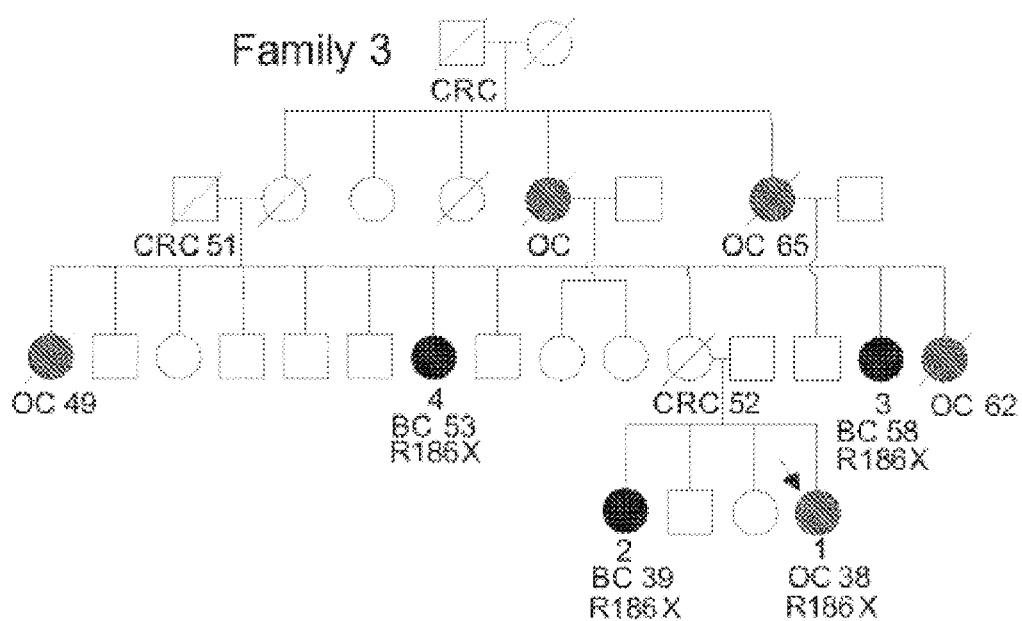
FIG. 1C. Abridged pedigree of a family with RAD51D.
Figure 1D:
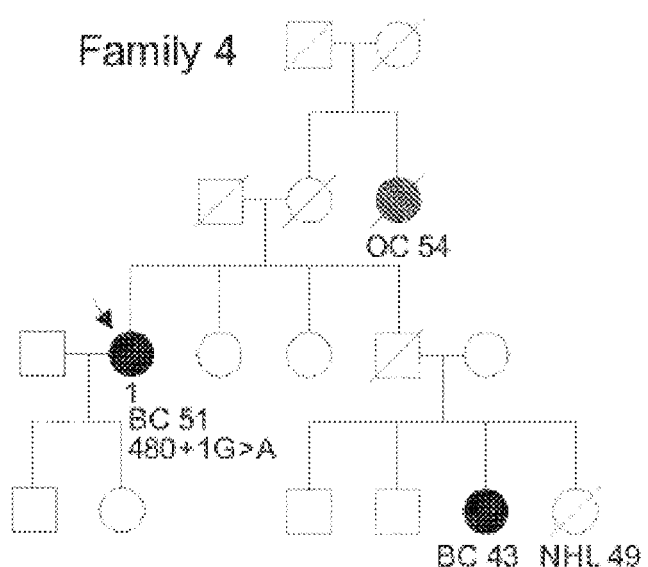
FIG. 1D. Abridged pedigree of a family with RAD51D.
Figure 1E:
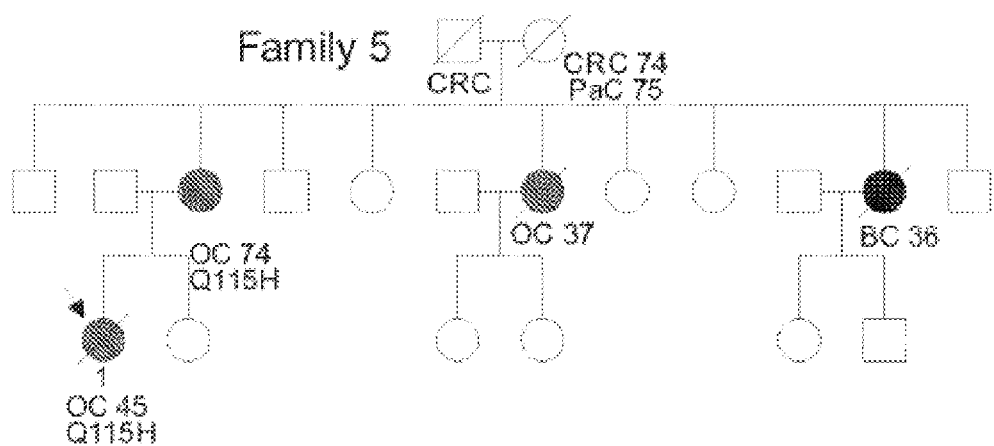
FIG. 1E. Abridged pedigree of a family with RAD51D.
Figure 1F:
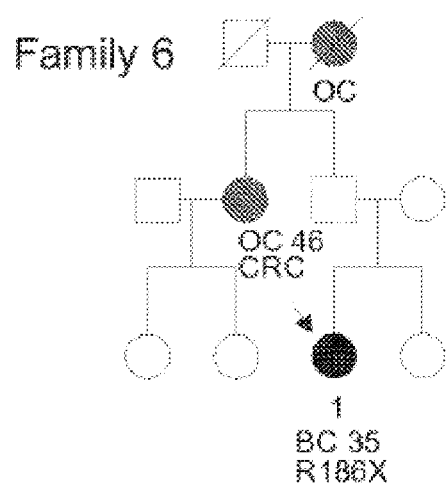
FIG. 1F. Abridged pedigree of a family with RAD51D.
Figure 1G:
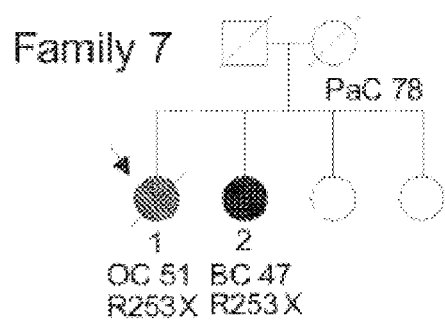
FIG. 1G. Abridged pedigree of a family with RAD51D.
Figure 1H:
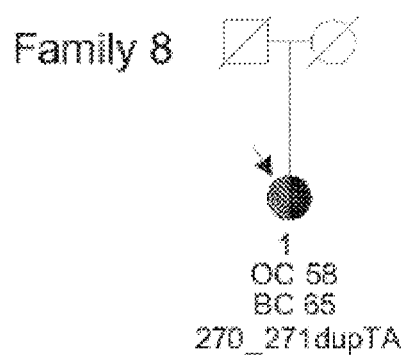
FIG. 1H. Abridged pedigree of a family with RAD51D.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

As used herein, unless explicitly stated otherwise or clearly implied otherwise the term 'about' refers to a range of values plus or minus 10 percent, e.g. about 1.0 encompasses values from 0.9 to 1.1.

As used herein, unless explicitly stated otherwise or clearly implied otherwise the terms 'therapeutically effective dose,' 'therapeutically effective amounts,' and the like, refers to a portion of a compound that has a net positive effect on the health and well being of a human or other animal. Therapeutic effects may include an improvement in longevity, quality of life and the like these effects also may also include a reduced susceptibility to developing disease or deteriorating health or well being. The effects may be immediate realized after a single dose and/or treatment or they may be cumulative realized after a series of doses and/or treatments.

As used herein unless explicitly noted or clearly intended otherwise, the term 'homology' as applied to polynucleotides refers to 3 nucleic acid long Condons that, while not identical to one another encode the same information when transcribed into proteins. For a further discussion of this term as it is used in regards to polynucleotides please see, Elliot and Elliot, *Biochemistry and Molecular Biology*, pages 293-295, published in 1997 by Oxford University Press, New York, N.Y., this portion of which is hereby incorporated herein by reference in its entirety.

As used herein unless explicitly noted or clearly intended otherwise, the term 'homology' as applied to polypeptides refers to amino acids commonly found in living organisms that are considered to be similar to one another in size, structure, and chemical reactivity. For a further discussion of this term as it is used in regards to polypeptides please see, Stryer, L., *Biochemistry*, $2^{nd}$ edition, pages 13-17, copyright 1981, published by W. H. Freeman and Company, San Francisco, Calif. this portion of which is hereby incorporated herein by reference in its entirety.

The inventors have found that mutations in the gene encoding RAD51D (a gene also known as RAD51L3) are associated with increased incidences of cancer, in particular ovarian cancer. Their studies are among the first to demonstrate (through a case-control mutation study) that mutations in RAD51D predispose humans to developing cancer.

It is estimated that 0.6% of unselected individuals with ovarian cancer will harbour inactivating RAD51D mutations. As genetic testing becomes more routine, such individuals will become more readily identifiable. This will allow such individuals to take advantage of regular monitoring for cancer development; suitable measures to prevent cancer development; and early use of suitable treatment in incidences where cancer occurs.

In light of the above, it will be recognised that the methods and kits of the invention are of particular utility in the context of ovarian cancer. For example, methods in accordance with the first aspect of the invention are well suited to use in determining that an individual is susceptible to ovarian cancer. Methods in accordance with the second aspect of the invention are well suited to predicting a likelihood of a human subject developing ovarian cancer; while methods in accordance with the third and fourth aspects of the invention are well suited to the treatment of ovarian cancer. Similarly, methods in accordance with the fifth aspect of the invention, involving genotyping of a human subject, may be of benefit in the identification of individuals who will benefit from regular cancer screening and/or preventative measures intended to avoid cancer formation or development.

In some embodiments, the cancer may be a cancer other than breast cancer.

In some embodiments of the methods of the first aspect of the invention, the human subject and the individual are one and the same. Thus in accordance with this embodiment the method provides an indication that an individual is susceptible to cancer based upon the presence of mutations in RAD51D-encoding nucleic acid molecules from the individual in question.

In some further embodiments, include treating of patients that have a heighted risk of developing ovarian cancer in order to reduce the likelihood that the individual will develop cancer or to quickly initiate treatment for cancer linked to the genetic markers disclosed herein. In some embodiments the markers identified in a first individual or a first group of individual is used to suggest treatment and/or monitoring for cancer, especially ovarian cancer, in individuals or groups of individuals that are related to the first individuals or groups or individuals. In accordance with these embodiments the methods provide an indication that an individual is susceptible to cancer based upon the presence of mutations in RAD51D-encoding nucleic acid molecules from a human subject who is a familial relative of the individual in question. As illustrated here, relatives with mutations will be, on average, at an approximately six fold increased risk of ovarian cancer, which equates to a ~10% cumulative risk by age 80. An indication of susceptibility to cancer produced by a method in accordance with this embodiment may subsequently be directly confirmed by a method in which the human and subject are one and the same (as described in the preceding paragraph).

An individual identified as being susceptible to cancer, or at increased likelihood of developing cancer, via a method in accordance with the present invention may additionally, or alternatively, then undergo assessment to detect whether or not cancer is present and if the patient is a good candidate for therapeutic intervention. In the case that the individual is found to have cancer then suitable cancer treatment may be initiated. Suitable treatment may include the methods of treatment of the third or fourth aspects of the invention, as discussed elsewhere in the specification.

An individual identified as being susceptible to cancer, or at increased likelihood of developing cancer, via a method in accordance with the present invention, but who has not developed cancer, may benefit from a rigorous monitoring approach to allow early detection of cancer. Such rigorous monitoring may incorporate increased incidences of checks for the development or presence of cancer (as compared to the regimen of checks that would be recommended for an individual perceived to be at "normal" risk). In a suitable embodiment a method of the invention may further comprise monitoring an individual, identified as being susceptible to cancer, for the development of cancer.

An individual identified as being susceptible to cancer, or at increased likelihood of developing cancer, via a method in accordance with the present invention may also take suitable preventative measures to avoid cancer development. In the case of individuals identified as being at risk of ovarian cancer, such suitable preventative measures may include laparoscopic oophorectomy.

"Methods of treatment" in accordance with the third aspect of the invention make use of DNA damaging agents or TOPO I inhibitors to effect treatment of individuals identified as being at a heightened risk for developing cancers such as ovarian cancer by the identification of certain genetic markers found to exit within the individual by use of the methods, kits, and/or systems disclosed herein. Examples of DNA damaging agents suitable for use in accordance with these methods of treatment include: platinum-based therapeutic agents such as carboplatin (which may be used with our without the microtubule stabiliser paclitaxel), and cisplatin. Examples of TOPO I inhibitors suitable for use in accordance with these methods of treatment include: Campothecin, Topotecan, and Irinotecan.

The methods of treatment of the fourth aspect of the invention make use of PARP inhibitors. Examples of PARP include Iniparib (previously BSi 201), Olaparib (previously AZD-2281), ABT-888 (Veliparib), G014699 CEP 9722 MK 4827 KU-0059436 (AZD2281) LT-673, PJ34, 3-aminobenzamide. The data described in the Examples indicate that the PARP inhibitor Olaparib is particularly effective in causing the death of cells that have an inactivating mutation of RAD51D.

As set out in the Examples, inactivation of RAD51D renders cells particularly sensitive to treatment with PARP inhibitors, and so treatment of cancer with such PARP inhibitors may also be a preferred embodiment of cancer treatment referred to in connection with other methods or aspects of the invention. That said, in suitable embodiments any of the DNA damaging agents or TOPO I inhibitors referred to above may additionally or alternatively be utilised in the treatment of cancer referred to in connection with other methods or aspects of the invention.

"RAD51D-Encoding Nucleic Acid Molecules"

The skilled artisan will readily be able to identify suitable RAD51D-encoding nucleic acid molecules suitable for use in accordance with the invention. For instance, the RAD51D gene represents a suitable example of such a nucleic acid. Thus in suitable embodiments of the invention the nucleic acid molecule is genomic DNA.

Alternatively, the nucleic acid molecule may be a nucleic acid molecule indicative of gene expression within the human subject. Accordingly, in suitable embodiments of the invention the nucleic acid molecule is mRNA.

The skilled artisan will be well aware of suitable methods by which genomic DNA and/or mRNA may be obtained from a sample from a human subject. The skilled artisan will also be aware of suitable methods by which genomic DNA and/or mRNA nucleic acid molecules may be assayed for the presence of a mutation. Details of suitable methods for obtaining and assaying samples are described elsewhere in the specification.

The methods of the invention may make use of any suitable sample that provides information regarding RAD51D-encoding nucleic acids within the human subject. In a suitable embodiment the sample may comprise biological cells from the human subject. By way of example, a suitable sample may comprise lymphocytes from the human subject, or cells from the human subject's buccal cavity. It will be appreciated that in embodiments where the sample comprises lymphocytes, the sample may be a blood sample from the human subject. In embodiments where the sample comprises cells from the buccal cavity, the sample may be collected by means of an oral swab or buccal rinse.

In suitable embodiments the sample may comprise a tumour sample. Examples of suitable samples of this sort include tumour biopsies. Thus ovarian cancer tumour biopsies may be utilised in methods of the invention in which the cancer is ovarian cancer.

"Inactivating Mutations"

The inventors have found inactivating mutations in RAD51D-encoding nucleic acid molecules to be useful in the methods or kits of the invention. For the purposes of the present disclosure, an "inactivating mutation" in such a nucleic acid may be taken as being any mutation in said nucleic acid molecule that prevents the production of functional RAD51D.

Since truncation of the RAD51D protein will prevent its' function, a suitable inactivating mutation may be one that prevents the production of full length RAD51D. It will be appreciated that, although nucleic acid molecules, such as the RAD51D gene, are referred to in the present disclosure as "RAD51D-encoding", when an inactivating mutation is present this means that functional RAD51D is not, in fact, properly encoded.

The inactivating mutation in the RAD51D-encoding nucleic acid molecule may be a germline mutation. Such germline mutations will be carried in cells throughout the human subject, thus allowing the methods of the invention to be practiced using samples comprising cells from tissues other than those believed to be at risk of cancer.

The skilled artisan will be aware of a range of techniques by which it may be determined whether a mutation found in a RAD51D-encoding nucleic acid molecule is, or is not, inactivating. In silico analysis techniques suitable for such use are described in the Examples of the present specification. Alternatively, suitable techniques may make use of in vitro or in vivo analysis in which mutant forms of RAD51D are assessed for their ability to exert a biological activity.

The inventors have identified a number of inactivating mutations associated with cancer, and in particular with ovarian cancer. These represent useful mutations that may be employed in the context of the methods of the invention and the kits of the invention.

Specific Useful Mutations of RAD51D

The following mutations have been found to have particularly strong association with ovarian cancer. Accordingly, the mutations are considered "useful" in the terms of the present invention on account of their suitability for use in accordance with the various aspects of the invention.

The nucleotide sequence of a cDNA encoding wild type human RAD51D is set out in SEQ ID NO.: 1, and the amino acid sequence of wild type human RAD51D is set out in SEQ ID NO.: 2. Except for where the context requires otherwise, references to wild type RAD51D protein should be taken as referring to the protein set out in SEQ ID NO.: 2, and SEQ ID NO.: 1 should be taken as a suitable illustrative example of a RAD51D-encoding nucleic acid.

As a first example of a useful mutation, the inventors have identified a deletion of adenine at position 363 of SEQ ID NO.: 1 (a mutation also referred to herein as c.363delA) that is associated with ovarian cancer. This mutation leads to a frameshift causing truncation of the encoded RAD51D protein.

A second useful mutation identified by the inventors comprises a substitution of guanine with adenine at position 803 of SEQ ID NO.: 1. This mutation (referred to herein as c.803G>A) leads to a truncation of the encoded RAD51D protein at the tryptophan residue at position 268 of SEQ ID NO.: 2 (a truncation also referred to p.Trp268X).

A third useful mutation identified by the inventors comprises a substitution of cytosine with thymine at position 556 of SEQ ID NO.: 1. This mutation (referred to herein as c.556C>T) leads to a truncation of the encoded RAD51D protein at the arginine residue at position 186 of SEQ ID NO.: 2 (a truncation also referred to as p.Arg186X). This c.556C>T mutation is viewed as being of particular importance in view of its' elevated prevalence in the results described in the Examples.

A fourth useful mutation identified by the inventors comprises an intronic substitution of guanine with adenine at position +1 after nucleotide 480 of the cDNA of SEQ ID NO.: 1. This mutation is also referred to as c.480+1G>A, and leads to a splicing defect causing truncation of the encoded RAD51D protein.

A fifth useful mutation identified by the inventors comprises a substitution of guanine with cytosine at position 345 of SEQ ID NO.: 1 (a mutation referred to as c.345G>C). This mutation is located at the final base of exon 4, and disrupts the splice site and results in skipping of exons 3 and 4. The mutation results in a substitution of glutamine with histidine at position 115 of the RAD51D protein encoded by nucleic acids comprising this mutation (a substitution also referred to as p.Gln115His).

A sixth useful mutation identified by the inventors comprises a substitution of cytosine with thymine at position 757 of SEQ ID NO.: 1 (a mutation also referred to as c.757C>T). This mutation leads to a truncation of the encoded RAD51D protein at the arginine residue at position 253 of SEQ ID NO.: 2 (a truncation also referred to as p.Arg253X).

A seventh useful mutation identified by the inventors comprises a duplication of the thymine and adenine bases found at positions 270 and 271 of SEQ ID NO.: 1 (a mutation also referred to as c.270-271dupTA), resulting in a frameshift that causes truncation of the encoded RAD51D protein.

The mutations described above are inactivating mutations, and each is associated with ovarian cancer.

The inventors have also identified an eighth inactivating mutation comprising a deletion of cytosine at position 748 of SEQ ID NO.: 1 (also referred to as c.748delC) which they also believe to be useful in the context of the present invention. This mutation was identified in a population control, and the cancer status of the individual carrying this mutation is not known. However, it is the inventors' opinion that the inactivating nature of this RAD51D mutation is such that it may be utilised in the methods of the invention, and represents a suitable mutation that may be targeted for amplification by oligonucleotides provided in kits of the invention.

In view of the above, it will be appreciated that, in a suitable embodiment, a method of the invention may involve assaying a sample for the presence of one or more mutations independently selected from the group consisting of: c.363delA; c.803G>A; c.556C>T; c.480+1G>A; c.345G>C; c.757C>T; c.270-271dupTA; and optionally c.748delC.

The methods of the invention may further comprise assaying a sample from the human subject for a further nucleic acid mutation associated with susceptibility to cancer. In suitable embodiments the nucleic acid mutation may be a mutation in a gene associated with susceptibility to ovarian cancer. For example, suitable methods in accordance with such an embodiment may further comprise assaying a sample from the human subject for a mutation in one or more genes independently selected from the group consisting of: BRCA1; BRCA2; MSH2, MLH1, MSH6, BRIP1, and RAD51C and/or one or more single nucleotide polymorphisms (SNPs) selected from the group consisting of: rs2072590 (found at locus 2q31); rs2665390 (found at locus 3q25); rs10088218 (found at locus 8q24); rs3814113 (found at locus 9p22); rs9303542 (found at locus 17q21); and rs2363956 (found at locus 19p13).

In an alternative embodiment the nucleic acid mutation may be a mutation in a gene associated with susceptibility to breast or ovarian cancer. For example, suitable methods in accordance with such an embodiment may further comprise assaying a sample from the human subject for a mutation in one or more genes independently selected from the group consisting of: BRCA1; BRCA2; MSH2, MLH1, MSH6, BRIP1, RAD51C TP53, PTEN, ATM, PALB2, CHEK2, STK11, and CDH1 and/or one or more single nucleotide polymorphisms (SNPs) selected from the group consisting of: rs2072590 (found at locus 2q31); rs2665390 (found at locus 3q25); rs10088218 (found at locus 8q24); rs3814113 (found at locus 9p22); rs9303542 (found at locus 17q21); and rs2363956 (found at locus 19p13).

The SNPs referred to above are disclosed in K. L. Bolton, et al.; Journal of International Medicine, 2012, 271; 366-378, the disclosure of which is hereby incorporated by reference.

In suitable embodiments, the methods of the invention may be practiced in respect of an individual known to be negative for mutations in BRCA1 and BRCA2.

Assaying for the Presence of a Mutation

The various aspects of the invention involve assaying a nucleic acid sample for the presence of a mutation. It will be appreciated that many suitable assaying methods are known to those of skill in the art, and that suitable examples of such methods may be utilised in order to practice the methods of the invention. Merely by way of example, the methods of the invention may be put into practice using an assaying method able to determine the DNA sequence of the RAD51D gene, or part thereof, of a subject. Suitable techniques are described in greater detail in the Examples.

Assays for the presence of mutations in RAD51D-encoding nucleic acid molecules, or complements thereof, may utilise methods in which some, or all, of the RAD51D gene is amplified. Such amplified nucleic acids corresponding to the RAD51D gene, or fragments thereof, may then be sequenced by methods known to those skilled in the art.

The polymerase chain reaction (PCR) represents a suitable technique by which nucleic acids may be amplified in order to facilitate their sequencing. In suitable embodiments the assaying used in methods of the invention may comprise a step of generating amplified nucleic acid molecules comprising an inactivating mutation in the region encoding RAD51D. Such amplified nucleic acid molecules may comprise one or more of the mutations selected from the group consisting of: c.363delA; c.803G>A; c.480+1G>A; c.345G>C; c.556C>T; c.757C>T; c.270-271dupTA; and optionally c.748delC. The amplified nucleic acid molecules may further be isolated prior to subsequent use.

In suitable embodiments amplified and/or isolated nucleic acid molecules comprising one or more mutations in the RAD51D-encoding region may be sequenced in order to determine the presence or absence of such mutations.

Suitable oligonucleotide primers that may be used to amplify RAD51D-encoding nucleic acid molecules comprising a mutation may be selected from the group set out in Table 2.

Generally the assaying will be practiced in vitro. The assaying may be practiced using a kit in accordance with the sixth aspect of the invention, or a system in accordance with the seventh aspect of the invention.

In a suitable embodiment, a kit of the invention may comprise oligonucleotides capable of amplifying some, or all, of the RAD51D gene. Merely by way of example, suitable oligonucleotides may be capable of amplifying the full coding sequence and intron/exon boundaries of RAD51D. As described below, examples of such oligonucleotides include the primers set out in Table 2. In embodiments in which all, or substantially all, of the RAD51D gene is amplified, any inactivating mutations present may thus be amplified.

In a suitable embodiment, a kit of the invention may comprise oligonucleotides capable of amplifying one or more mutations independently selected from the group consisting of: c.363delA; c.803G>A; c.480+1G>A; c.345G>C; c.556C>T; c.757C>T; c.270-271dupTA; and optionally c.748delC. Suitable kits may include oligonucleotides capable of amplifying each of these recited mutations. In suitable embodiments the oligonucleotides are capable of amplifying the entire RAD51D-encoding region comprising the recited mutation(s). In alternative embodiments the oligonucleotides are capable of amplifying a portion of the RAD51D-encoding nucleic acid comprising the recited mutation(s). In a suitable embodiment the oligonucleotides are capable of specifically amplifying a portion of the RAD51D-encoding nucleic acid comprising the recited mutation(s).

In a suitable embodiment a kit in accordance with the sixth aspect of the invention may comprise oligonucleotides selected from the group consisting of SEQ ID NOS. 3-24, which are the primers set out in Table 2.

Systems for Determining Predisposition to Cancer

The seventh aspect of the invention provides systems that may be used in determining a subject's predisposition to cancer. Systems comprising the same elements may also be of use in other methods of the invention, such as the methods of the second, third, fourth, and fifth aspects of the invention.

The systems of the invention make use of a sample analyzer able to determine the RAD51D gene status in a sample from the subject. Suitable analyzers that may be employed in such systems will be known to those of skill in the art. In a suitable embodiment an ABI3730 automated sequencer (ABI Perkin Elmer) will represent an example of a sequence analyzer that may be used in these aspects of the invention. Such a sequence analyzer may be used in conjunction with the commercially available BIGDYE TERMINATOR Cycle sequencing kit.

The systems of the invention may also comprise means for the production of amplified nucleic acids comprising a mutation, such as an inactivating mutation, in a region encoding RAD51D. The systems of the invention may further comprise means for the isolation of such nucleic acids.

The systems of the invention also utilise computer programs, which receive RAD51D gene status data, and compare RAD51D gene status from the sample with a reference. Both of these functions may be served by a single computer program, or alternatively separate first and second computer programs may be used. Suitable examples of computer programs that may be used in accordance with these aspects of the invention will be apparent to those of skill in the art. Merely by way of example, Mutation Surveyor software (www.softgenetics.com) may be used to analyse sequencing traces, and represents a suitable example of a single computer program that may be used in such embodiments.

In suitable embodiments, the sequencer and/or computer programs used in systems in accordance with the invention are able to respectively sequence a RAD51D-encoding nucleic acid (such as an amplified nucleic acid comprising a mutation) and identify the presence of a mutation within the nucleic acid. In a suitable embodiment the program is capable of identifying the presence of a mutation and determining whether the mutation is an inactivating mutation, such as a mutation giving rise to a truncation of the encoded protein. Merely by way of example, such a determination may involve identification of the presence of an inserted stop codon, frameshift, or duplication as compared to the wild type nucleic acid sequence (such as SEQ ID NO: 1).

In suitable embodiments, the effects of RAD51D missense variants on protein function may be predicted using PolyPhen and SIFT software. All variants (intronic and coding) may be analysed for their potential effect on splicing. In the first instance, variants may be analysed using two splice prediction algorithms NNsplice and MaxEntScan, via the Alamut software interface (Interactive Biosoftware). If both NNsplice and MaxEntScan scores were altered by >20% (i.e. a wildtype splice-site score decreases and/or a cryptic splice-site score increases) three further prediction algorithms may be utilised; NetGene2, HumanSplicingFinder, and Genscan. In such an embodiment, a consensus decrease in a wildtype splice-site score and/or a consensus increase in a cryptic splicer-site score across all algorithms will be considered indicative of disruption of normal splicing.

While the methods, kits, and systems of the invention are claimed, and have been exemplified, with reference to the relationship between cancer (such as ovarian cancer) and inactivating mutations in nucleic acids encoding RAD51D, the inventors do not wish to preclude the possibility that non-inactivating mutations may also be indicative of susceptibility to cancer. Accordingly, the invention also provides a method of determining that an individual is susceptible to cancer, the method comprising assaying a sample comprising a RAD51D-encoding nucleic acid molecule, or a complement thereof, from a human subject for the presence of a non-inactivating mutation in said nucleic acid, wherein the presence of a non-inactivating mutation in the nucleic acid indicates that the individual is susceptible to cancer.

EXAMPLES

Recently RAD51C mutations were identified in families with breast and ovarian cancer. The following study was undertaken to investigate the role of RAD51D in cancer susceptibility. We identified eight inactivating RAD51D mutations in unrelated individuals from 911 breast-ovarian cancer families compared with one in 1060 controls (P=0.01). The association was principally with ovarian cancer with three mutations identified in the 59 pedigrees with three or more ovarian cancer cases (P=0.0005). The relative risk of ovarian cancer for RAD51D mutation carriers was estimated to be 6.30 (95% CI: 2.86-13.85; P=4.8× $10^{-6}$). By contrast, the relative risk of breast cancer was estimated to be 1.32 (95% CI: 0.59-2.96; P=0.50). These data indicate that RAD51D mutation testing may have clinical utility in individuals with ovarian cancer and their families. Moreover, we show that cells deficient in RAD51D are sensitive to treatment with a PARP inhibitor, suggesting a possible therapeutic approach for cancers arising in RAD51D mutation carriers.

The full coding sequence and intron-exon boundaries of RAD51D in DNA from unrelated probands from 911 breast-ovarian cancer families and 1060 population controls was sequenced (Table 2). The breast-ovarian cancer families included at least one case of breast cancer and at least one case of ovarian cancer and all were negative for mutations in BRCA1 and BRCA2 (Table 3).

Inactivating mutations in RAD51D in eight of 911 cases and one of 1060 controls (P=0.01) were identified (Table 1). Referring now to FIGS. 1A-1H. These schematic figures show abridged pedigrees of eight families with RAD51D mutations. Individuals with ovarian cancer are shown as shaded circles, individuals with breast cancer are shown as black circles, other cancers are shown as unfilled circles or squares. Where known, the age of cancer diagnosis is under the individual, with two ages given for metachronas bilateral breast cancers. The relevant RAD51D mutation is given under the affected individuals analysed but not the unaffected individuals, to preserve confidentiality. BC, breast cancer; BC bilat., bilateral breast cancer; OC, ovarian cancer; CRC, colorectal cancer; LC, lung cancer; NHL, non-Hodgkin lymphoma; PaC, pancreatic cancer; Pr, prostate cancer.

TABLE 1 ancer history and pathology in RAD51D mutation carriers

| Family ID | Mutation* | Person ID | Cancer history (age at which cancer occurred, in years) | Pathology | Tumor analysis |
|---|---|---|---|---|---|
| FAM1 | c.363delA | 1 | Breast cancer, left (34) | Invasive ductal carcinoma of no special type, grade 3 | NA |
| | | | Breast cancer, right (52) | Invasive ductal carcinoma of no special type, grade 3 | Loss of wildtype allele |
| FAM2 | c.803G > A; W268X | 1 | Ovarian cancer (58) | Bilateral serous adenocarcinoma | Loss of wildtype allele |
| FAM3 | c.556C > T; R186X | 1 | Ovarian cancer (38) | NA | NA |
| | | 2 | Breast cancer (39) | High grade ductal comedo carcinoma in situ | NA |
| | | 3 | Breast cancer (58) | Invasive carcinoma with medullary features | NA |
| | | 4 | Breast cancer (53) | Invasive ductal carcinoma of no special type | NA |
| FAM4 | c.480 + 1G > A | 1 | Breast cancer (51) | Invasive ductal carcinoma of no special type, grade 3 | NA |

TABLE 1-continued

Cancer history and pathology in RAD51D mutation carriers

| Family ID | Mutation* | Person ID | Cancer history (age at which cancer occurred, in years) | Pathology | Tumor analysis |
|---|---|---|---|---|---|
| FAM5 | c.345G > C; Q115H** | 1 | Ovarian cancer (45) | Bilateral serous adenocarcinoma | NA |
| | | 2 | Ovarian cancer (74) | NA | NA |
| FAM6 | c.556C > T; R186X | 1 | Breast cancer (35) | Invasive ductal carcinoma of no special type, grade 3 | NA |
| FAM7 | c.757C > T; R253X | 1 | Ovarian cancer (51) | Differentiated endometrioid adenocarcinoma | NA |
| | | 2 | Breast cancer (47) | NA | NA |
| FAM8 | c.270_271dupTA | 1 | Ovarian cancer (58) | Differentiated adenocarcinoma | Loss of mutant allele |
| | | | Breast cancer (65) | Invasive ductal carcinoma of no special type, grade 3 | Reduction of wildtype allele |
| Control | c.748delC | | NA | NA | NA |

*Mutation nomenclature corresponds to Ensembl Transcript ID ENST00000345365
**This mutation is at the final base of exon 4, disrupts the splice-site and results in skipping of exons 3 and 4. Person IDs correspond to FIG. 1.
NA: not available.

The mutations were not equally distributed within the series, with a higher prevalence in families with more than one ovarian cancer; four mutations were detected in 235 families with two or more cases of ovarian cancer (P=0.005) and three mutations were detected in the 59 families with three or more cases of ovarian cancer (P=0.0005) (FIG. 1).

Figure 4:
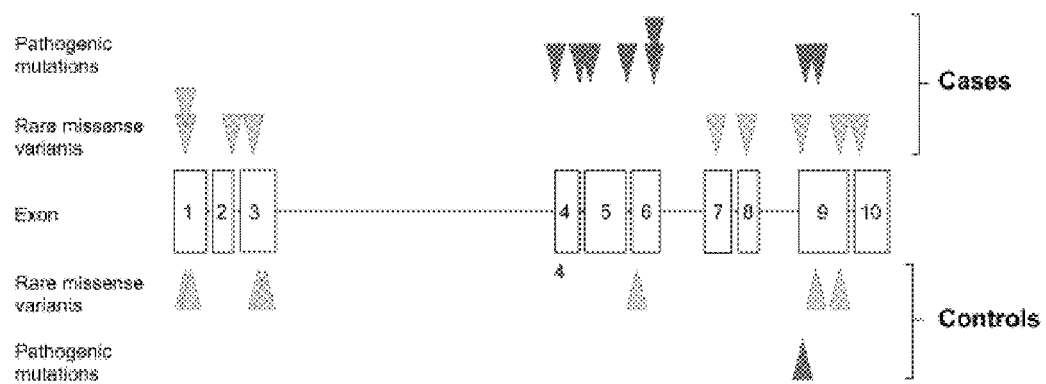
FIG. 4. Schematic showing the distribution of RAD51D pathogenic mutation and rare missense variants.

All the mutations are predicted to result in protein truncation through frameshifting insertions or deletions (n=3), the generation of nonsense codons (n=4) or splice defects (n=2) (Table 1). Five intronic, 3 synonymous and 15 non-synonymous variants were identified. Three coding variants, rs9901455 (S78S), rs4796033 (R165Q) and rs28363284 (E233G) have minor allele frequency>1% and no association was observed for any of these variants (Table 4). Of the remaining rare variants, three were present in both cases and controls, nine were detected in a single case and eight were detected in a single control (Table 5). There was thus no overall difference in the frequency of non-truncating RAD51D variants between cases and controls. Moreover, there was no difference in the position or predicted functional effects of these variants and it is noteworthy that an equal number (n=5) of non-synonymous variants detected in cases and controls are predicted to affect function (FIG. 4 and Table 5). These data indicate that mutations that result in inactivation of RAD51D function predispose to cancer, but that variants with less significant functional effects are likely to be non-pathogenic.

TABLE 4

RAD51D variants identified with minor allele frequency >1%.

| | | BC/OC | | Controls | | | In silico analyses | | |
|---|---|---|---|---|---|---|---|---|---|
| Mutation | dbSNP | No. alleles (n = 1822) | Freq. | No. alleles (n = 2120) | Freq. | P Value | SIFT prediction | Polyphen prediction | Consensus splice prediction |
| 234C > T_S78S | rs9901455 | 124 | 0.07 | 171 | 0.08 | 0.15 | — | — | Benign |
| 494G > A_R165Q | rs4796033 | 264 | 0.14 | 332 | 0.16 | 0.33 | Tolerated | Benign | Benign |
| 698A > G_E233G | rs28363284 | 43 | 0.02 | 45 | 0.02 | 0.67 | Tolerated | Probably damaging | Benign |

TABLE 5

Rare RAD51D variants identified.

| | No. of alleles in: | | | | Consensus |
|---|---|---|---|---|---|
| Mutation | BC/OC (n = 1822) | Controls (n = 2120) | SIFT prediction | Polyphen prediction | splice prediction |
| Non-synonymous | | | | | |
| 26G > C_C9S | 2 | 1 | Affects function* | Probably damaging | Benign |
| 40G > A_E14K | — | 1 | Tolerated | Benign | Benign |

TABLE 5-continued

Rare RAD51D variants identified.

| Mutation | No. of alleles in: BC/OC (n = 1822) | No. of alleles in: Controls (n = 2120) | SIFT prediction | Polyphen prediction | Consensus splice prediction |
|---|---|---|---|---|---|
| 137C > G_S46C | 1 | — | Affects function* | Probably damaging | Benign |
| 185C > T_S62L | 1 | — | Affects function* | Possibly damaging | Benign |
| 202G > A_G68S | — | 1 | Affects function* | Probably damaging | Benign |
| 233C > T_S78F | — | 1 | Affects function* | Possibly damaging | Benign |
| 493C > T_R165W | — | 1 | Affects function* | Probably damaging | Benign |
| 620C > T_S207L | 1 | — | Affects function* | Probably damaging | Benign |
| 695G > A_R232Q | 1 | — | Affects function* | Probably damaging | Benign |
| 753A > G_I251M | 1 | — | Tolerated | Benign | Benign |
| 793G > A_G265R | — | 1 | Affects function* | Probably damaging | Benign |
| 872G > A_R291H | 1 | 1 | Tolerated | Benign | Benign |
| 911G > A_G304D | 1 | — | Tolerated | Benign | Benign |
| Synonymous | | | | | |
| 630G > A_A210A | 1 | — | | | Benign |
| 900A > G_R300R | — | 1 | | | Benign |
| Non-coding | | | | | |
| 82 + 9G > A | — | 1 | | | Benign |
| 346-10C > T | 1 | — | | | Benign |
| 577-9T > G | 1 | — | | | Uncertain |
| 739-10T > C | 1 | 1 | | | Benign |
| 904-3C > T | — | 1 | | | Benign |

*low confidence prediction

Figure 5:
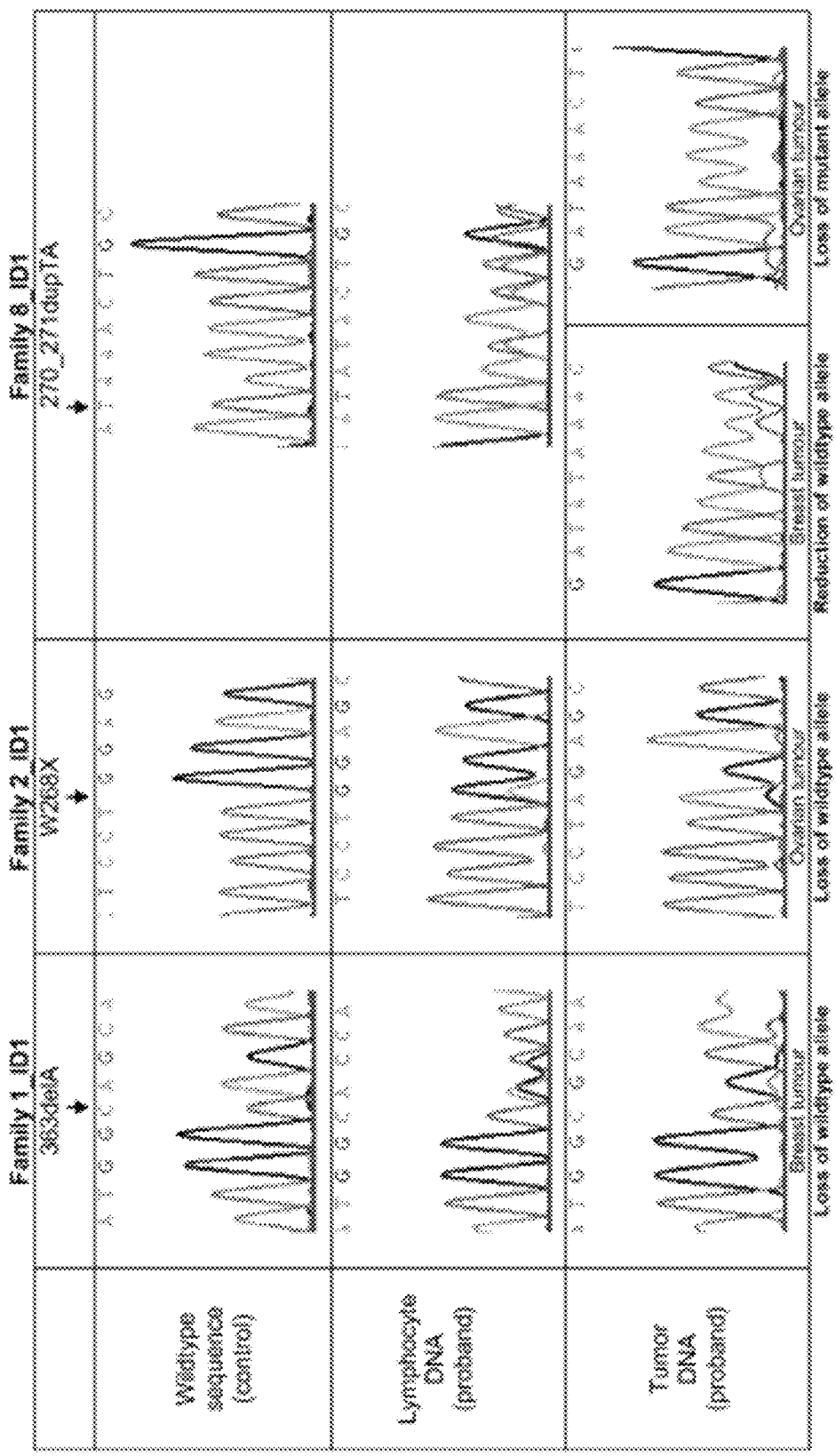
FIG. 5. Charts illustrating lymphocytes and tumor DNA analysis performed in individuals that harbour RAD51D mutations.

Family mutations were tested for in samples from 13 relatives. This analysis revealed that five of five individuals affected with ovarian or breast cancer carried the family mutation, whereas six of eight unaffected relatives did not carry the family mutation. Several other cancers were present in relatives, such as pancreatic, prostate and colorectal cancer (FIG. 1). However, the mutation status of these individuals is not known and additional studies will be required to evaluate whether RAD51D mutations predispose to other cancers. Pathology information was available for four ovarian cancers from RAD51D mutation carriers; three were serous adenocarcinoma and one was an endometrioid cancer. Pathology information was available for eight breast cancers of which seven were ductal in origin and one was a carcinoma with medullary features. Receptor status was available from five breast cancers of which three were estrogen receptor positive and two were negative. Tumour material was available from two ovarian cancers and two breast cancers. We detected loss of the wild-type allele in one ovarian and one breast cancer and reduction of the proportion of the wild-type allele in a further breast cancer. In the final ovarian cancer the mutant allele was lost and the wildtype allele was retained (Table 1 and FIG. 5).

Figure 2:
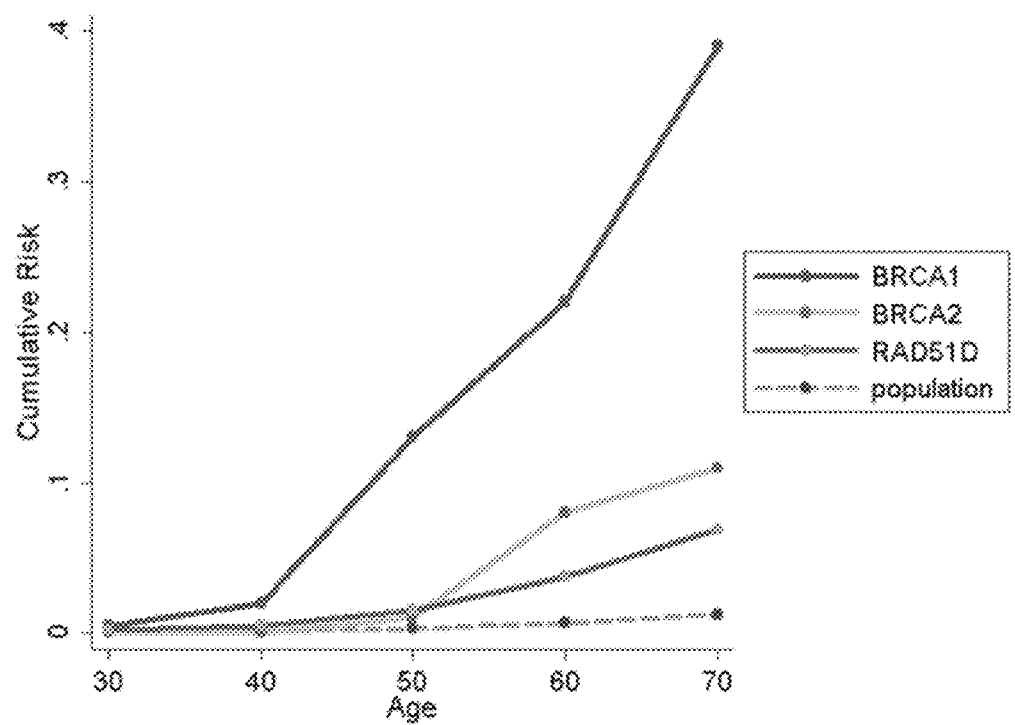
FIG. 2. Illustrates average age-related cumulative risk of ovarian cancer in RAD51D mutation carriers, BRCA1 and BRCA2 mutation carriers and the population.

These characteristics are typical of the intermediate-penetrance cancer predisposition genes that we, and others, have described in breast cancer. To estimate directly the risks associated with RAD51D mutations we undertook modified segregation analysis, by modelling the risks of ovarian and breast cancer simultaneously and incorporating the information from the controls and full pedigrees of both mutation-positive and mutation-negative breast-ovarian cancer families. The ovarian cancer relative risk for RAD51D mutation carriers was estimated to be 6.30 (95% CI: 2.86-13.85; $P=4.8 \times 10^{-6}$) (FIG. 2). By contrast, the association with breast cancer risk was not statistically significant (RR=1.32 (95% CI: 0.59-2.96; P=0.50).

To further explore the role of RAD51D mutations in breast cancer predisposition, the gene was sequenced in an additional series of 737 unrelated individuals from pedigrees in which there was familial breast cancer but no ovarian cancer. No inactivating mutations were identified (0/737 cases vs 1/1060 controls P=1.0). Although at first glance these data may seem surprising, they are consistent with the results of the segregation analysis. This is because if RAD51D mutations confer a sizeable relative risk of ovarian cancer but only a small, or no, increase in breast cancer risk, the frequency of RAD51D mutations in a series of breast cancer families selected on the basis of not containing ovarian cancer would be anticipated to be very low. The data are also consistent with the detection of RAD51D mutations in seven individuals with breast cancer in the breast-ovarian cancer families, as we specifically ascertained the ovarian cancer cases because of their close family history of breast cancer. This will inevitably result in an enrichment of breast cancer in relatives of RAD51D mutation-positive ovarian cancer cases, irrespective of whether such mutations confer a risk of breast cancer. To formally refine the risk of breast cancer associated with RAD51D mutations will likely be very challenging because the population frequency of RAD51D mutations is so low. Assuming a population mutation frequency of 0.1% and a relative risk of breast cancer of 1.3, full gene mutational analysis of RAD51D in 275,000 cases and 275,000 controls would be required to have 90% power to demonstrate the association.

These data clearly demonstrate that RAD51D is an ovarian cancer predisposition gene but further studies in familial and sporadic ovarian cancer series would be of value to further clarify the risks of ovarian cancer. RAD51D mutation analysis in individuals with Fanconi anemia and Fanconi-like disorders would also be of interest, given that biallelic mutations in BRCA2, PALB2, BRIP1 and RAD51C have been demonstrated to cause these phenotypes.

Figure 3A:
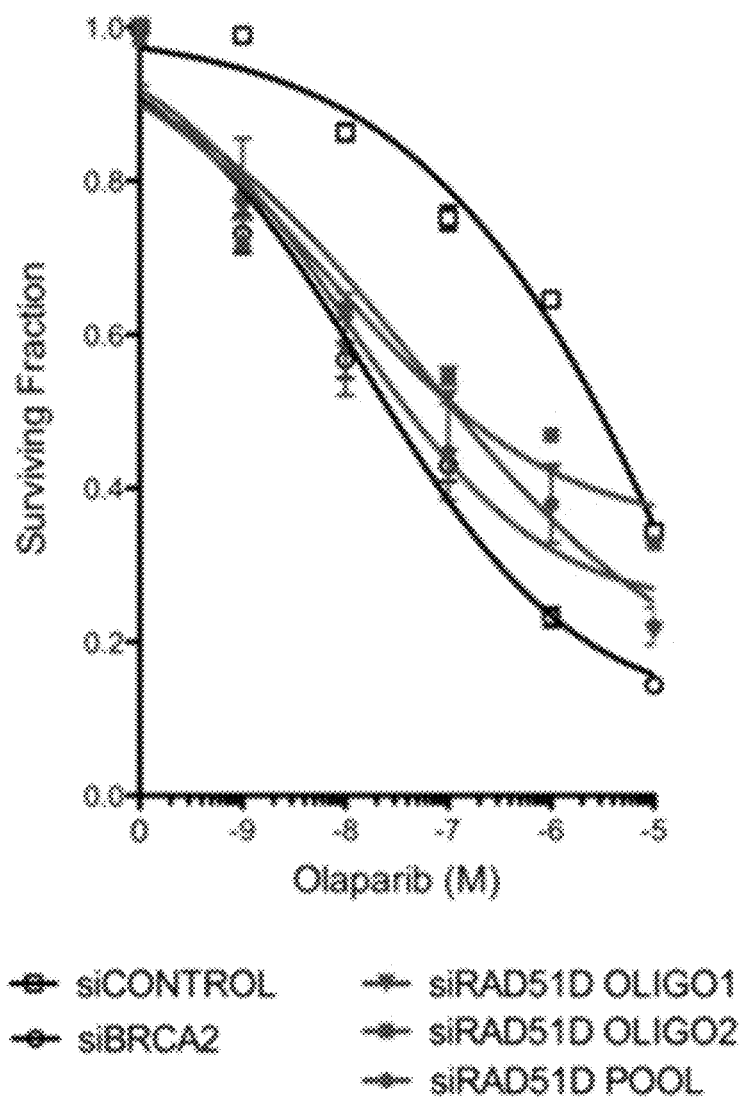
FIG. 3.A Graphic illustration of the effect of Olaparib concentration on Surviving Fraction, measured in siControl and siBRCA2.
Figure 3B:
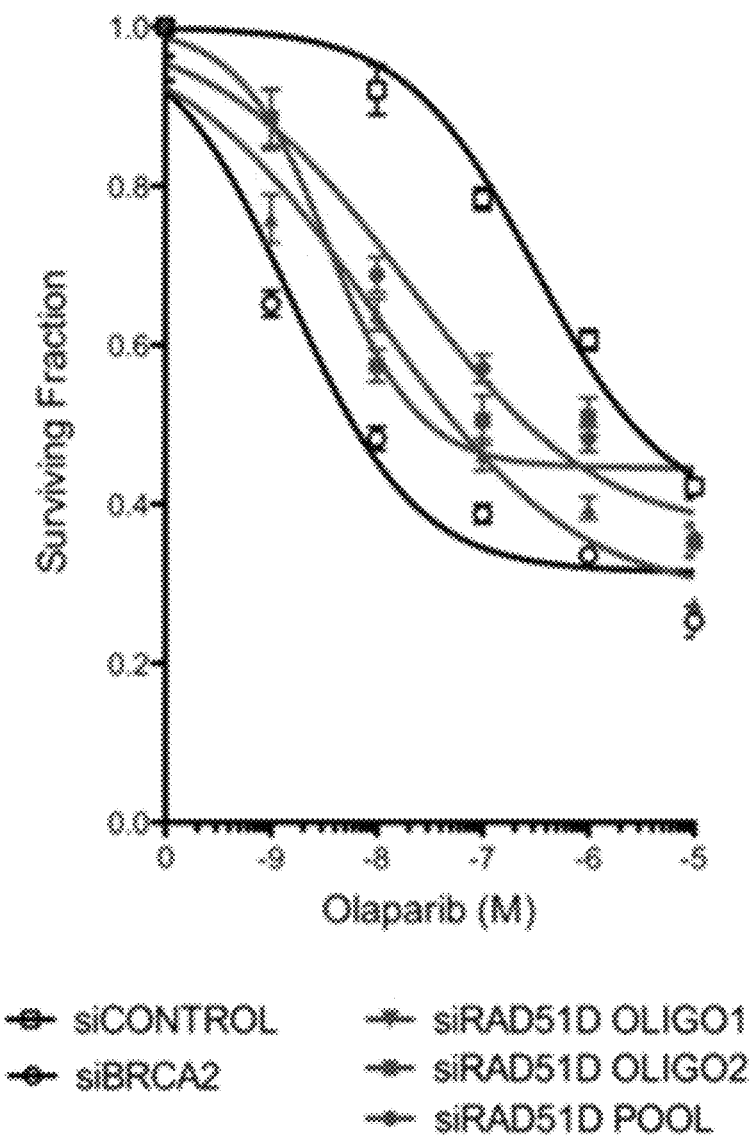
Figure 3C:
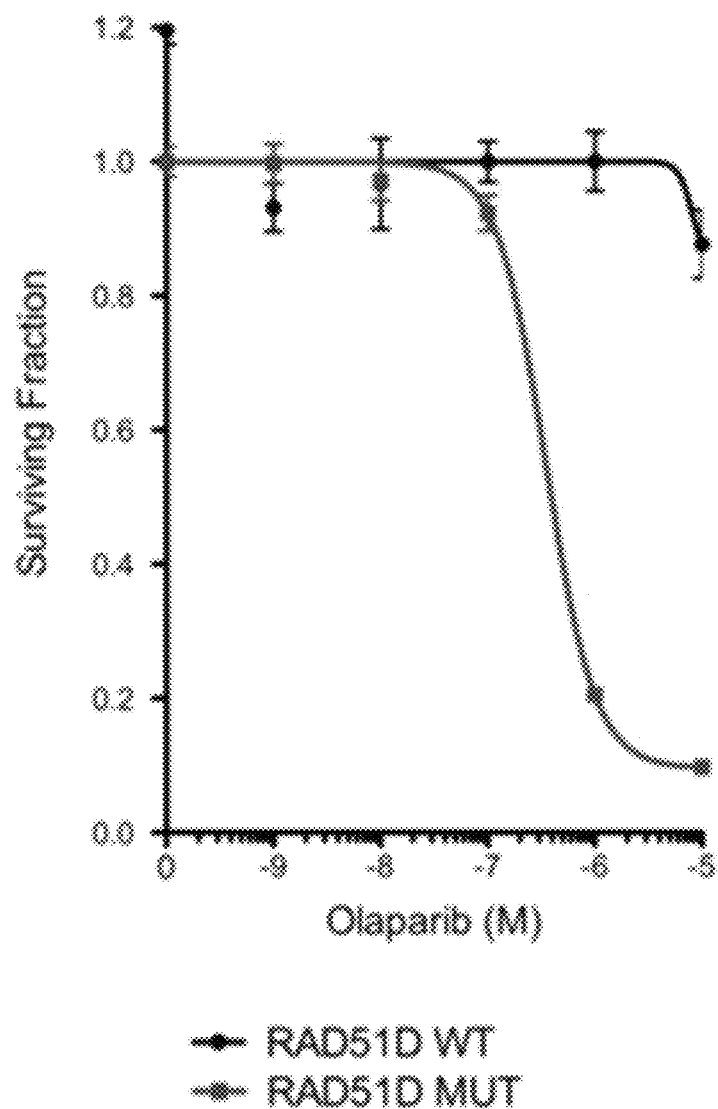

This method has clinical utility both for individuals with cancer and their relatives. Cancer patients with RAD51D mutations may benefit from specific therapies such as Poly (ADP-Ribose) Polymerase (PARP) inhibitors, which have shown efficacy in patients with impairment of HR due to mutations in BRCA1 or BRCA2. To investigate this we used RNA interference (RNAi) and assessed the relationship between RAD51D loss of function and the sensitivity of tumor cells to a clinical PARP inhibitor, olaparib (AstraZeneca) 4-[(3-[(4-cyclopropylcarbonyl)piperazin-4-yl]carbonyl)-4-fluorophenyl]methyl(2H)phthalazin-1-one. Referring now to FIG. 3. The effect of RAD51D silencing on olaparib sensitivity. CAL51 (FIG. 3A) or MCF7 (FIG. 3B) cells were transfected with siCONTROL, siRNA directed against RAD51D or siRNA directed against BRCA2 and then treated with olaparib for 7 days before assaying for cell viability. Wild-type CHO cells or CHO cells mutated in RAD51D were treated with olaparib for 7 days before assaying for cell viability (FIG. 3C).

Short interfering (si) RNAi reagents targeting RAD51D caused olaparib sensitivity of a magnitude similar to that achieved using silencing of BRCA2 (FIGS. 3A, B), an observation in keeping with the HR defect observed in RAD51D null rodent cell lines. To extend this analysis, we also observed the RAD51D selective effect of olaparib in RAD51D deficient CHO cells in which both alleles of RAD51D have been rendered dysfunctional by gene targeting (FIG. 3C). These data suggest that PARP inhibitors may have clinical utility in individuals with RAD51D mutations. An estimate based on these data is that only ~0.6% of unselected individuals with ovarian cancer will harbour RAD51D mutations, but as we enter an era in which genetic testing will become routine, such individuals will be readily identifiable. Their identification will also be of potential value to female relatives, as those with mutations will be on average at ~6 fold increased risk of ovarian cancer, which equates to an ~10% cumulative risk by age 80. An appreciable proportion of women at this level of risk may consider strategies such as laprascopic oophorectomy, which is well-tolerated and undertaken in many women with BRCA mutations.

Patients and Samples

Cases

Lymphocyte DNA from 1648 families with breast-ovarian cancer or breast cancer-only was used. These were ascertained from 24 genetics centres in the UK via the Genetics of Familial Breast Cancer Study (FBCS), which recruits women≥18 years who have had breast cancer and/or ovarian cancer and have a family history of breast cancer and/or ovarian cancer. At least 97% of families are of European ancestry. Index cases from each family were screened and negative for germline mutations, including large rearrangements, in BRCA1 and BRCA2. Informed consent was obtained from all participants and the research was approved by the London Multicentre Research Ethics Committee (MREC/01/2/18).

Breast-Ovarian Cancer Pedigrees

Some 911 unrelated index cases from breast-ovarian cancer pedigrees were used. The index cases were diagnosed with breast and/or ovarian cancer. Each family included an individual with both breast and ovarian cancer or included at least one case of breast cancer and at least one case of ovarian cancer with ≤1 intervening unaffected female relatives. Cases of ovarian cancer below the age of 20 were excluded from the analysis, as an appreciable proportion are likely to represent non-epithelial ovarian tumours, for example germ cell cancers. 271/911 probands had ovarian cancer (+/−breast cancer) and 617 probands had breast cancer only. The number of family members (including the probands) diagnosed with breast cancer and/or ovarian cancer, in the 911 breast-ovarian cancer pedigrees included in the analysis is illustrated in Table 3.

Breast Cancer-Only Pedigrees

Some 737 unrelated index cases from breast cancer-only pedigrees were included. The index case from each family was diagnosed with breast cancer, and had bilateral disease and/or a family history of breast cancer. There was no known case of ovarian cancer in any pedigree. The number of family members (including the probands) diagnosed with breast cancer, in the 737 breast cancer-only pedigrees included in the analysis is illustrated in Table 3. The six cases of isolated breast cancer all had bilateral disease.

TABLE 3

Number of breast and ovarian cancers in the breast-ovarian cancer families and the breast cancer-only families analysed for RAD51D mutations.

| | | Breast-ovarian cancer families | | | | | | Breast cancer-only families |
|---|---|---|---|---|---|---|---|---|
| | | Family members with ovarian cancer | | | | | | |
| | | 1 | 2 | 3 | 4 | ≥5 | Total | |
| Family members with breast cancer | 1 | 105 (3) | 47 (1) | 12 (1) | 1 | 1 | 166 | 6 |
| | 2 | 221 (1) | 58 | 10 | 0 | 1 | 290 | 58 |
| | 3 | 184 | 37 | 6 | 1 (1) | 3 (1) | 231 | 217 |
| | 4 | 80 | 17 | 6 | 1 | 2 | 106 | 223 |
| | ≥5 | 86 | 17 | 6 | 8 | 1 | 118 | 233 |
| | Total | 676 | 176 | 40 | 12 | 7 | 911 | 737 |

(Shaded cells indicate RAD51D +ve families)

Samples and Pathology Information from Mutation Positive Families

For families in which a mutation in RAD51D was detected, DNA samples from relatives and all obtainable samples were genotyped for the family mutation was sought. Tumor material, pathology information, and receptor status in probands and affected relatives was requested from the hospitals where they had been treated.

Controls

Lymphocyte DNA from 1060 population-based controls obtained from the 1958 Birth Cohort Collection was used, an ongoing follow-up of persons born in Great Britain in one week in 1958. Biomedical assessment was undertaken during 2002-2004 at which blood samples and informed consent were obtained for creation of a genetic resource but phenotype data for these individuals is not available. At least 97% of the controls were of European ancestry.

Mutation Analysis of RAD51D

Genomic DNA extracted from lymphocytes was analysed for mutations by direct sequencing of the full coding sequence and intron/exon boundaries of RAD51D. Primer sequences and PCR conditions are given in Table 2. The PCR reactions were performed in multiplex using the Qiagen Multiplex PCR Kit (Qiagen) according to the manufacturer's instructions. Amplicons were unidirectionally sequenced using the BIGDYE TERMINATOR Cycle sequencing kit and an ABI3730 automated sequencer (ABI Perkin Elmer). Sequencing traces were analysed using Mutation Surveyor software (www.softgenetics.com) and by visual inspection. All mutations were confirmed by bidirectional sequencing from a fresh aliquot of the stock DNA. Samples from members of RAD51D mutation-positive families were tested for the family mutation by direct sequencing of the appropriate exon.

TABLE 2

Primers and PCR conditions for RAD51D mutation analysis.

| Exon SEQ ID. NO | Primer sequence 5'-3' | | Size (bp) | Anneal. Temp (° C.) |
|---|---|---|---|---|
| | Forward | Reverse | | |
| Sequencing primers | | | | |
| 3-4 | GCCTCCTCCTCTCTCCTTTC | CACCCTTCCTGAGCCTCTC | 378 | 60 |
| 5-6 | GGGTAGAATTGACACCCCATT | TGACTTCTGACTCCAAGTGACC | 299 | 60 |
| 7-8 | AAAGGGAGCAGAGGGTTCTC | ATGTCCTGACCCCTTTCCTT | 366 | 60 |
| 9-10 | TGGCCAGTGATGTTCAAAGA | CCCATTAGTACGCTGAAGCTC | 298 | 60 |
| 11-12 | GGACTCAGCCCATTTGTGTT | AGCAAGTTTGAAGGCAAGGA | 351 | 60 |
| 13-14 | CTGAGTCCTTGCATCCAGGT | ATTGCACATCTGCATTTCCA | 300 | 60 |
| 15-16 | CTTGCTGTATTTGGGATGGG | TTTGGGGTTCAGAAGCTGAC | 498 | 60 |
| 17-18 | CTCTCCGTAAAATGAAGCGG | TAAACAGCAGGCGTTACTGG | 568 | 60 |

TABLE 2 -continued

Primers and PCR conditions for RAD51D mutation analysis.

| Exon SEQ ID. NO | Primer sequence 5'-3' | | Size (bp) | Anneal. Temp (° C.) |
|---|---|---|---|---|
| | Forward | Reverse | | |
| Internal primers for tumor analysis | | | | |
| 19-20 | CAGAACCAGTGCTTGAAAGAAA | GGCCTCACATGTACCTGAGTT | 199 | 68-50 |
| 21-22 | GAATCTGGGCAAGGTTTGGT | TGGGTTTTAGCCTGAAGCAG | 200 | 68-50 |
| 23-24 | AGGCCTCTGTTTTCCTCTCC | CGATGGTGTCCAGGAGAATC | 198 | 68-50 |

In Silico Analyses of Identified Variants

The predicted effects of RAD51D missense variants on protein function was computed using PolyPhen and SIFT. All variants (intronic and coding) were analysed for their potential effect on splicing. In the first instance, variants were analysed using two splice prediction algorithms NNsplice and MaxEntScan, via the Alamut software interface (Interactive Biosoftware). If both NNsplice and MaxEntScan scores were altered by >20% (i.e. a wildtype splice-site score decreases and/or a cryptic splice-site score increases) three further prediction algorithms were utilised; NetGene2, HumanSplicingFinder, and Genscan. A consensus decrease in a wildtype splice-site score and/or a consensus increase in a cryptic splicer-site score across all algorithms were considered indicative of disruption of normal splicing.

Tumor Analysis

Representative tumor sections were stained with nuclear fast red and microdissected using a sterile needle and a stereomicroscope (Olympus SZ61, Tokyo, Japan) to ensure the proportion of tumour cells was >90%, as previously described. DNA was extracted using the DNeasy kit (Qiagen) according to the manufacturer's instructions. DNA concentration was measured using the PicoGreen assay (Invitrogen), according to the manufacturer's instructions. RAD51D specific fragments encompassing the relevant mutations were PCR-amplified using the primers in Table 2, and bidirectionally sequenced using the BIGDYE TERMINATOR Cycle sequencing kit and an ABI3730 automated sequencer (ABI Perkin Elmer). Sequence traces from tumor DNA were compared to sequence traces from lymphocyte DNA from the same individual.

Drug Sensitivity

Non-silencing BRCA2 and RAD51D SIGENOME siRNAs (Dharmacon, Lafayette, Colo., USA) were used. CAL51 and MCF7 cells were grown in DMEM (Gibco, Invitrogen) supplemented with 10% (v/v) FCS (Gibco, Invitrogen). CHO RAD51D WT (51D1.3 clone) and CHO RAD51 dysfunctional (51D1 clone) cells were grown in αMEM (Gibco, Invitrogen) supplemented with 10% FCS (Gibco, Invitrogen). Cells were siRNA transfected using RNAiMAX (Invitrogen), plated in 96 well microtitre plates and then exposed to a titration of olaparib for 7 days. Media and drug was replenished every 3 days. After 7 days continuous culture, cell viability was estimated using Cell TitreGlo reagent (Promega Madison, Wis., USA) and surviving fractions calculated as previously described.

Statistical Methods

Statistical analyses were performed using STATA v11 software (StataCorp, College Station, Tex., USA). The frequency of mutations in cases and controls was compared using a two-sided Fisher's exact test. We estimated the RAD51D combined mutation frequency, the breast cancer risk ratio and the ovarian cancer risk ratio relative to non-RAD51D mutation carriers simultaneously using modified segregation analysis implemented in the pedigree analysis software MENDEL. The analysis was based on breast and ovarian cancer occurrence in the combined dataset of families and controls. All individuals were censored at age 80 years, the age of their first cancer or their age of death or last observation, whichever occurred first. Females who had had bilateral prophylactic mastectomy were censored for breast cancer, and those who had had bilateral prophylactic oophorectomy were censored for ovarian cancer. Thus, only information on the first cancer was included in the primary analysis. In this analysis it was assumed that the breast incidence depends on the underlying genotype through a model of the form: $\lambda(t)=\lambda_0(t)\exp(\beta x)$ where $\lambda_0(t)$ is the baseline incidence at age t in non-mutation carriers, $\beta$ is the log risk ratio associated with the mutation and x takes value 0 for non-mutation carriers and 1 for mutation carriers. A similar model was assumed for the ovarian cancer incidences. Breast and ovarian cancers were assumed to occur independently, conditional on the genotype. The overall breast and ovarian cancer incidences were constrained to agree with the population incidences for England and Wales in the period of 1993-1997, as described previously. The models were parameterised in terms of the mutation frequencies and log-risk ratios for breast and ovarian cancer. Parameters were estimated using maximum likelihood estimation. Since RAD51D mutation screening was carried out in all index cases and controls we were able to incorporate information from all controls and the full pedigrees from all cases (including those without a RAD51D mutation) together with the segregation information from the families in which a RAD51D mutation was detected and genotyping was possible in relatives of the index case. To adjust for ascertainment, we modelled the conditional likelihood of all family phenotypes and mutation status of the index family member and other tested family members, given the disease phenotypes of all family members. For the controls we modelled the likelihood of the mutation status given they were unaffected. The variances of the parameters were obtained by inverting the observed information matrix. Log risk ratios were assumed to be normally distributed. Because this model does not explicitly incorporate the effects of other susceptibility genes, it assumes implicitly that the effects of RAD51D and other potential susceptibility genes can be regarded as independent, as in a multiplicative model.

Power calculations were based on two-sided association testing with a significance level of $\alpha=0.05$. It was assumed that the observed frequency of truncating (i.e. inactivating)

mutations in cases from breast-ovarian cancer families (0.88%) and controls (0.094%) reflects the true underlying mutation frequencies in the population, and that the effect calculated from the segregation analysis (OR=6.30) represents the true risk of ovarian cancer in the population. It was assumed that the same ratio of truncating mutations:missense variants (predicted deleterious) would be detected in isolated cases of ovarian cancer as cases from breast-ovarian cancer families. It was assumed that in association testing of mutation frequencies across 25,000 genes that the $\chi 2$ statistics will be normally distributed and we applied a Bonferroni correction for multiple testing.

```
Sequence information
RAD51D transcript and protein sequences
Name: RAD51D-001
Transcript ID: ENST00000345365
Length (bp): 2404
Protein ID: ENSP00000338790
Length (aa): 328
Biotype: Protein coding
CCDS: CCDS11287
cDNA
```

KEY

Codons          Alternating codons    Alternating codons
Exons           Alternating exons     Alternating exons
Other features  UTR

SEQ ID NO.: 1

```
   1 CTGGAACCCGGAAGCGGCAGCGCGGCGCGACCCGGCGCGCGGGCTCTGGGCGCGGGAATC

61 CCGGCGGATCCCGGGCGGGCGGATGACCCCCAGCCCTACCCTTGGTGCCGCCTCCTCCTC

121 TCTCCTTTCTCCTCCGGCAGCCAGCGCGCCTGTGTCCTCTCTAGGAAGGGGTAGGGGAGG

181 GGCGTCTGGAGAGGACCCCCCGCGAATGCCCACGTGACGTGCAGTCCCCCTGGGGCTGTT

241 CCGGCCTGCGGGGAACATGGGCGTGCTCAGGGTCGGACTGTGCCCTGGCCTTACCGAGGA

301 GATGATCCAGCTTCTCAGGAGCCACAGGATCAAGACAGTGGTGGACCTGGTTTCTGCAGA

361 CCTGGAAGAGGTAGCTCAGAAATGTGGCTTGTCTTACAAGGCCCTGGTTGCCCTGAGGCG

421 GGTGCTGCTGGCTCAGTTCTCGGCTTTCCCCGTGAATGGCGCTGATCTCTACGAGGAACT

481 GAAGACCTCCACTGCCATCCTGTCCACTGGCATTGGCAGTCTTGATAAACTGCTTGATGC

541 TGGTCTCTATACTGGAGAAGTGACTGAAATTGTAGGAGGCCCAGGTAGCGGCAAAACTCA

601 GGTATGTCTCTGTATGGCAGCAAATGTGGCCCATGGCCTGCAGCAAAACGTCCTATATGT

661 AGATTCCAATGGAGGGCTGACAGCTTCCCGCGTCCTCCAGCTGCTTCAGGCTAAAACCCA

721 GGATGAGGAGGAACAGGCAGAAGCTCTCCGGAGGATCCAGGTGGTGCATGCATTTGACAT

781 CTTCCAGATGCTGGATGTGCTGCAGGAGCTCCGAGGCACTGTGGCCCAGCAGGTGACTGG

841 TTCTTCAGGAACTGTGAAGGTGGTGGTTGTGGACTCGGTCACTGCGGTGGTTTCCCCACT

901 TCTGGGAGGTCAGCAGAGGGAAGGCTTGGCCTTGATGATGCAGCTGGCCCGAGAGCTGAA

961 GACCCTGGCCCGGGACCTTGGCATGGCAGTGGTGGTGACCAACCACATAACTCGAGACAG

1021 GGACAGCGGGAGGCTCAAACCTGCCCTCGGACGCTCCTGGAGCTTTGTGCCCAGCACTCG
```

-continued

```
1081 GATTCTCCTGGACACCATCGAGGGAGCAGGAGCATCAGGCGGCCGGCGCATGGCGTGTCT
1141 GGCCAAATCTTCCCGACAGCCAACAGGTTTCCAGGAGATGGTAGACATTGGGACCTGGGG
1201 GACCTCAGAGCAGAGTGCCACATTACAGGGTGATCAGACATGACCTGTGCTGTTGTTTGG
1261 GAAACAGGGAAGCATTGGGGACCCCTCCCAACTTTTCTTCCCAGTAACGCCTGCTGTTTA
1321 CTGCCACCTGGCACTGGTGACTACAGACGTTCTCAGGCTGGCCAGAAGAGACATCTTGGG
1381 TTCCTTGGCCTCACTCTCTGTAAGCATATAAACCACAGGCGAAAGAGGATGCTGCATTGC
1441 GAGGACCCAGAAATTCATACTGGTGCCACGTTTCCTTCCCTTATTTCTAACGTGTATGTT
1501 TCTGGTGGAAACCAAGTTCACCCTGGCTGGGAGCATCTCTGATGAGGCATGCTGGCGACT
1561 GGATGGATAATCCTGTGCATCACCATTGTGTCCTGTGCTCCCTCCTAGCGCAGTGGCCAA
1621 GCCGGGAAAGCCTCTAACTTGCCTTTGCTGCTGCTGCCTTTTTTTCTTTTGTCTCTGCC
1681 TTTCCATTTGTTAGATGGGGGCCCACTCTTCCTTAGCTCTGTCTCTGAGTTACTGGGTGG
1741 AAATAAGCTTATAAATGAAATACTCTTCTTCATCTCTGTTTTGCTCTTAAAAATATAAAA
1801 AGGCAATTCCCCGAGCCCTAGAGCCACCTGATTTCCCCTTAGAAGGCTGTTTTTCAGTTT
1861 CCCCCAGTGAGGCCCAAAGAACAGTTTATTCCTCCTTTCCTCTTGCTGATTTGGTTTCAG
1921 ACCTGCCTGCATCACCATGACTAGGTGAGAACGTGTGGGCTCGCTGCAGTTCCAGGGATA
1981 TAATTTAACAGAAAGGGAGGGTATGACCTGCTCCTGGTGAATCCAGCCACTCATTTAATA
2041 TGCATGGTGCCCTGTGGGGCCCCTCCACAGTACAGCATAACCAGAGGTGCTGAACCATGG
2101 CCTTGCCCATAAACAGACAGAGGAGAATTTGCACAGTAAATAGAGCCAGCTGGGAAAATT
2161 GATGCTGACGTAAATAATACATGGCAAATCTAGTCCTTTATGCAGAAAATTCATTGCTGGT
2221 GGCTCCAAGATGCAATATAATTACACCTCTCTTCCTGCCAGCTGTACCACAGCTAGTGCC
2281 CTAGTGTATGAAATAATCCCTCTGTCTTTCACCAGCACTGTGGCCATCCGTCTGAGAGCC
2341 ATGACCCTGGCTGGGAGGGGACGAAGACACCAGGGAATGGAAAATAAAAGGAAAAGTACA
2401 GAAA
```

Protein

KEY: Exons | Alternating exons | Alternating exons | Residue overlap splice site

SEQ ID NO.: 2

MGVLRVGLCPGLTEEMIQLLRSHRIKTVVDLVSADLEEVAQKCGLSYKALVALRRVLLAQ

FSAPPVNGADLYEELKTSTAILSTGIGSLDKLLDAGLYTGEVTEIVGGPGSGKTQVCLCM

AANVAHGLQQNVLYVDSNGGLTASRLLQLLQAKTQDEEEQAEALPRIQVVHAFDIFQMLD

VLQELRGTVAQQVTGSSGTVKVVVVDSVTAVVSPLLGGQQREGLALMMQLARELKTLARD

LGMAVVVTNHITRDRDSGRLKPALGRSWSPVPSTRILLDTIEGAGASGGRRMACLAKSSR

QPTGFQEMVDIGTWGTSEQSATLQGDGQT cDNA and Protein

```
                                  KEY
   Codons       [Alternating codons] [Alternating codons]
   Exons        [Alternating exons]  [Alternating exons]
   Variations    5 prime UTR          3 prime UTR         Non-synonymous coding
                 splice site          Stop gained         Synonymous coding
   Other features UTR
```

```
                              W
  1  CTGGAACCCGGAAGCCGGCAGCGCGGCGCGACCCGGCGGGCGGGCTCTGGGCGCGGGAATC

................................
        ................................
 61  CCGGCGGATCCCGGGCGGGCGGATGACCCCCAGCCCTACCCTTGGTGCCGCCTCCTCCTC

................................
        ................................
                                                              K
121  TCTCCTTTCTCCTCCGGCAGCCAGCGCGCCTGTGTCCTCTCTAGGAAGGGGTAGGGGAGG

................................
        ................................
                                        K
181  GGCGTCTGGAGAGGACCCCCCGCGAATGCCCACGTGACGTGCAGTCCCCCTGGGGCTGTT

................................
        ................................
                                    S                 S
241  CCGGCCTGCGGGGAACATGGGCGTGCTCAGGGTCGGACTGTGCCCTGGCCTTACCGAGGA
                    ATGGGCGTGCTCAGGGTCGGACTGTGCCCTGGCCTTACCGAGGA
                    -M--G--V--L--R--V--G--L-=C=-P--G--L--T--E--E
                              K          M
301  GATGATCCAGCTTCTCAGGAGCCACAGGATCAAGACAGTGGTGGACCTGGTTTCTGCAGA
 45  GATGATCCAGCTTCTCAGGAGCCACAGGATCAAGACAGTGGTGGACCTGGTTTCTGCAGA
 15  --M--I--Q--L--L--R--S--H--R=-I--K-=T=-V--V--D--L--V--S--A--D
                      R              Y                      R
361  CCTGGAAGAGGTAGCTCAGAAATGTGGCTTGTCTTACAAGGCCCTGGTTGCCCTGAGGCG
105  CCTGGAAGAGGTAGCTCAGAAATGTGGCTTGTCTTACAAGGCCCTGGTTGCCCTGAGGCG
 35  --L--E--E--V--A--Q--K--C--G--L--S--Y--K-=A=-L--V--A--L--R-=R
                                  R           R      Y
421  GGTGCTGCTGGCTCAGTTCTCGGCTTTCCCCGTGAATGGCGCTGATCTCTACGAGGAACT
165  GGTGCTGCTGGCTCAGTTCTCGGCTTTCCCCGTGAATGGCGCTGATCTCTACGAGGAACT
 55  =-V--L--L--A--Q--F--S--A--P--P-=V=-N--G--A-=D=--L--Y--E--E--L
              Y
481  GAAGACCTCCACTGCCATCCTGTCCACTGGCATTGGCAGTCTTGATAAACTGCTTGATGC
225  GAAGACCTCCACTGCCATCCTGTCCACTGGCATTGGCAGTCTTGATAAACTGCTTGATGC
 75  --K--T--S--T--A--I--L--S--T--G--I--G--S--L--D--K--L--L--D--A
            Y
541  TGGTCTCTATACTGGAGAAGTGACTGAAATTGTAGGAGGCCCAGGTAGCGGCAAAACTCA
285  TGGTCTCTATACTGGAGAAGTGACTGAAATTGTAGGAGGCCCAGGTAGCGGCAAAACTCA
 95  --G--L--Y--T--G--E--V--T--E--I--V--G--G--P--G--S--G--K--T--Q
                                      W
601  GGTATGTCTCTGTATGGCAGCAAATGTGGCCCATGGCCTGCAGCAAAACGTCCTATATGT
345  GGTATGTCTCTGTATGGCAGCAAATGTGGCCCATGGCCTGCAGCAAAACGTCCTATATGT
115  --V--C--L--C--M--A--A--N--V--A-=H=-G--L--Q--Q--N--V--L--Y--V
```

```
                  R                      R    Y
 661 AGATTCCAATGGAGGGCTGACAGCTTCCCGCCTCCTCCAGCTGCTTCAGGCTAAAACCCA
 405 AGATTCCAATGGAGGGCTGACAGCTTCCCGCCTCCTCCAGCTGCTTCAGGCTAAAACCCA
 135 --D--S-=N--G--G--L--T--A--S-=R=-L--L--Q--L--L--Q--A--K--T--Q

S                  N            R
 721 GGATGAGGAGGAACAGGCAGAAGCTCTCCGGAGGATCCAGGTGGTGCATGCATTTGACAT
 465 GGATGAGGAGGAACAGGCAGAAGCTCTCCGGAGGATCCAGGTGGTGCATGCATTTGACAT
 155 --D-=E=-E--E--Q--A--E--A--L-=R=-R--I--Q--V--V--H--A--F--D--I

R                                        R
 781 CTTCCAGATGCTGGATGTGCTGCAGGAGCTCCGAGGCACTGTGGCCCAGCAGGTGACTGG
 525 CTTCCAGATGCTGGATGTGCTGCAGGAGCTCCGAGGCACTGTGGCCCAGCAGGTGACTGG
 175 --F--Q--M--L--D--V--L--Q--E--L--R--G--T--V-=A=-Q--Q--V--T--G

R                                  Y
 841 TTCTTCAGGAACTGTGAAGGTGGTGGTTGTGGACTCGGTCACTGCGGTGGTTTCCCCACT
 585 TTCTTCAGGAACTGTGAAGGTGGTGGTTGTGGACTCGGTCACTGCGGTGGTTTCCCCACT
 195 --S--S--G--T--V--K--V--V--V-=V=-D--S--V--T--A--V--V--S--P--L

R   R          R  R
 901 TCTGGGAGGTCAGCAGAGGGAAGGCTTGGCCTTGATGATGCAGCTGGCCCGAGAGCTGAA
 645 TCTGGGAGGTCAGCAGAGGGAAGGCTTGGCCTTGATGATGCAGCTGGCCCGAGAGCTGAA
 215 --L--G--G--Q--Q--R--E--G--L-=A=-L--M--M--Q--L--A-=P==E==L--K

S
 961 GACCCTGGCCCGGGACCTTGGCATGGCAGTGGTGGTGACCAACCACATAACTCGAGACAG
 705 GACCCTGGCCCGGGACCTTGGCATGGCAGTGGTGGTGACCAACCACATAACTCGAGACAG
 235 --T--L--A--R--D--L--G--M--A--V--V--V--T--N--H--I--T-=R=-D--R

YR                  R
1021 GGACAGCCGGGAGGCTCAAACCTGCCCTCGGACGCTCCTGGAGCTTTGTGCCCAGCACTCG
 765 GGACAGCCGGGAGGCTCAAACCTGCCCTCGGACGCTCCTGGAGCTTTGTGCCCAGCACTCG
 255 --D--S-=+G=-R--L--K--P--A--L-=G=-R--S--W--S--F--V--P--S--T--R

Y  K       RY
1081 GATTCTCCTGGACACCATCGAGGGAGCAGGAGCATCAGGCGGCCGGCGCATGGCGTGTCT
 825 GATTCTCCTGGACACCATCGAGGGAGCAGGAGCATCAGGCGGCCGGCGCATGGCGTGTCT
 275 --I--L--L--D--T--I--E--G--A--G--A--S--G-=G=-R-=R=-M--A--C--L

N            W            K
1141 GGCCAAATCTTCCCGACAGCCAACAGGTTTCCAGGAGATGGTAGACATTGGGACCTGGGG
 885 GGCCAAATCTTCCCGACAGCCAACAGGTTTCCAGGAGATGGTAGACATTGGGACCTGGGG
 295 --A--K--S--S--R--Q--P--R--G--F--Q-=E=-M--V--D-=I=-G--T--W-=G

R       R                         Y
1201 GACCTCAGAGCAGAGTGCCACATTACAGGGTGATCAGACATGACCTGTGCTGTTGTTTGG
 945 GACCTCAGAGCAGAGTGCCACATTACAGGGTGATCAGACATGA................
 315 =-T--S--E--Q--S--A--T--L--Q--G--D--Q-=T=-*-................
1261 GAAACAGGGGAAGCATTGGGACCCCTCCCAACTTTTCTTCCCAGTAACGCCTGCTGTTTA

..........................................
         ..........................................
                              YR     R               M
1321 CTGCCACCTGGCACTGGTGACTACAGACGTTCTCAGGCTGGCCAGAAGAGACATCTTGGG

..........................................
         ..........................................
                                           Y
1381 TTCCTTGGCCTCACTCTCTGTAAGCATATAAACCACAGGCCGAAAGAGGATGCTGCATTGC

..........................................
         ..........................................
1441 GAGGACCCAGAAAATTCATACTGGTGCCACGTTTCCTTCCCTTATTTCTAACGTGTATGTT

..........................................
         ..........................................
          R
1501 TCTGGGTGGAAACCAAGTTCACCCTGGCTGGGAGCATCTCTGATGAGGCATGCTGGCGACT

..........................................
```

```
                                          NN   R
1561 GGATGGATAATCCTGTGCATCACCATTGTGTCCTGTGCTCCCTCCTAGCCCAGTGGCCAA

1621 GCCGGGAAAGCCTCTAACTTGCCCTTTGCTGCTGCTGCCTTTTTTTTCTTTTGTCTCTGCC

Y
1681 TTTCCATTTGTTAGATGGGGGCCCACTCTTCCTTAGCTCTGTCTCTGAGTTACTGGGTGG

R
1741 AAATAAGCTTATAAATGAAATACTCTTCTTCATCTCTGTTTTGCTCTTAAAAATATAAAA

1801 AGGCAATTCCCCGAGCCCTAGAGCCACCTGATTTCCCCTTAGAAGGCTGTTTTTCAGTTT

1861 CCCCCAGTGAGGCCCAAAGAACAGTTTATTCCTCGTTTCCTCTTGCTGATTTGGTTTCAG

N   R
1921 ACCTGCCTGCATCACCATGACTAGGTGAGAACGTGTGGGCTCGCTGCAGTTCCAGGGATA

1981 TAATTTAACAGAAAGGGAGGGTATGACCTGCTCCTGGTGAATCCAGCCACTCATTTAATA

Y
2041 TGCATGGTGCCCTGTGGGCCCCTCCACAGTACAGCATAACCAGAGGTGCTGAACCATGG

2101 CCTTGCCCATAAACAGACAGAGGAGAATTTGCACAGTAAATAGAGCCAGCTGGGAAAATT

Y
2161 GATGCTGACGTAAATAATACATGGCAAATCTAGTCCTTTATGCAGAAATTCATTGCTGGT

2221 GGCTCCAAGATGCAATATAATTACACCTCTCTTCCTGCCAGCTGTACCACAGCTAGTGCC

Y                        Y       Y
2281 CTAGTGTATGAAATAATCCCTCTGTCTTTCACCAGCACTGTGGCCATCCGTCTGAGAGCC

M
2341 ATGACCCTGGCTGGGAGGGGACGAAGACACCAGGGAATGGAAAATAAAAGGAAAAGTACA

2401 GAA
```

Referring now to FIG. 4. A schematic representation of RAD51D, showing the distribution of pathogenic mutations and rare missense variant identified in breast-ovarian cancer family and controls, Exons of RAD51D are shown as boxes, Pathogenic mutations, i.e., those predicated to result in premature protein truncation, are shown as red triangles and rare missense variant as blue triangles. Two mutation (C9S and R186X) were identified twice in cases and are thus depicted as two triangles one above the other.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

I claim:

1. A method of detecting one or more inactivating mutations in a person suspected of having ovarian cancer, comprising the steps of:
   providing a sample of blood, cells, or tissue from the person suspected of having ovarian cancer; and
   detecting one or more inactivating mutations in SEQ ID NO.:1, wherein the inactivating mutation is selected from the group consisting of: c.363delA; c.803G>A; c.480+1G>A; c.345G>C; c.556C>T; c.757C>T; c.270-271dupTA; and c.748delC.

2. The method of claim 1, wherein the step of detecting one or more inactivating mutations includes contacting at least one portion of SEQ ID NO.:1 with at least one molecule that hybridizes to at least one portion of SEQ ID NO.:1.

3. The method of claim 2, wherein the at least one molecule that hybridizes to at least one portion of SEQ ID NO:1 is at least one polynucleotide having at least 90 percent identity with at least one of the polynucleotides selected from the group consisting of: SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17, SEQ ID NO.: 18, SEQ ID NO.: 19, SEQ ID NO.: 20, SEQ ID NO.: 21, SEQ ID NO.: 22, SEQ ID NO.: 23, and SEQ ID NO.: 24.

* * * * *

```
                        SEQUENCE LISTING

<160> NUMBER OF SEQ ID NOS: 24

<210> SEQ ID NO 1
<211> LENGTH: 2404
<212> TYPE: DNA
<213> ORGANISM: homo sapiens

<400> SEQUENCE: 1
ctggaacccg gaagcggcag cgcggcgcga cccggcgggc gggctctggg cgcgggaatc      60
ccggcggatc ccgggcgggc ggatgacccc cagccctacc cttggtgccg cctcctcctc     120
tctcctttct cctccggcag ccagcgcgcc tgtgtcctct ctaggaaggg gtagggagg      180 ggcgtctgga gaggaccccc cgcgaatgcc cacgtgacgt gcagtccccc tggggctgtt     240
ccggcctgcg gggaacatgg gcgtgctcag ggtcggactg tgccctggcc ttaccgagga     300
gatgatccag cttctcagga gccacaggat caagacagtg gtggacctgg tttctgcaga     360
cctggaagag gtagctcaga aatgtggctt gtcttacaag gccctggttg ccctgaggcg     420
ggtgctgctg gctcagttct cggctttccc cgtgaatggc gctgatctct acgaggaact     480
gaagacctcc actgccatcc tgtccactgg cattggcagt cttgataaac tgcttgatgc     540
tggtctctat actggagaag tgactgaaat tgtaggaggc ccaggtagcg gcaaaactca     600
ggtatgtctc tgtatggcag caaatgtggc ccatggcctg cagcaaaacg tcctatatgt     660
agattccaat ggagggctga cagcttcccg cctcctccag ctgcttcagg ctaaaaccca     720
ggatgaggag gaacaggcag aagctctccg gaggatccag gtggtgcatg catttgacat     780
cttccagatg ctggatgtgc tgcaggagct ccgaggcact gtggcccagc aggtgactgg     840
ttcttcagga actgtgaagg tggtggttgt ggactcggtc actgcggtgg tttccccact     900
tctgggaggt cagcagaggg aaggcttggc cttgatgatg cagctggccc gagagctgaa     960
gaccctggcc cgggaccttg gcatggcagt ggtggtgacc aaccacataa ctcgagacag    1020
ggacagcggg aggctcaaac ctgccctcgg acgctcctgg agctttgtgc ccagcactcg    1080
gattctcctg gacaccatcg agggagcagg agcatcaggc ggccggcgca tggcgtgtct    1140
ggccaaatct tcccgacagc caacaggttt ccaggagatg gtagacattg ggacctgggg    1200
gacctcagag cagagtgcca cattacaggg tgatcagaca tgacctgtgc tgttgtttgg    1260
gaaacaggga agcattgggg acccctccca acttttcttc ccagtaacgc ctgctgttta    1320
ctgccacctg gcactggtga ctacagacgt tctcaggctg gccagaagag acatcttggg    1380
ttccttggcc tcactctctg taagcatata aaccacaggc gaaagaggat gctgcattgc    1440
gaggacccag aaattcatac tggtgccacg tttccttccc ttatttctaa cgtgtatgtt    1500 tctggtgaa accaagttca ccctggctgg gagcatctct gatgaggcat gctggcgact    1560
ggatggataa tcctgtgcat caccattgtg tcctgtgctc cctcctagcg cagtggccaa    1620
```

```
gccgggaaag cctctaactt gcctttgctg ctgctgcctt ttttttcttt tgtctctgcc   1680
tttccatttg ttagatgggg gcccactctt ccttagctct gtctctgagt tactgggtgg   1740
aaataagctt ataaatgaaa tactcttctt catctctgtt ttgctcttaa aaatataaaa   1800
aggcaattcc ccgagcccta gagccacctg atttcccctt agaaggctgt ttttcagttt   1860
cccccagtga ggcccaaaga acagtttatt cctcctttcc tcttgctgat ttggtttcag   1920
acctgcctgc atcaccatga ctaggtgaga acgtgtgggc tcgctgcagt tccagggata   1980
taatttaaca gaaagggagg gtatgacctg ctcctggtga atccagccac tcatttaata   2040
tgcatggtgc cctgtggggc ccctccacag tacagcataa ccagaggtgc tgaaccatgg   2100
ccttgcccat aaacagacag aggagaattt gcacagtaaa tagagccagc tgggaaaatt   2160
gatgctgacg taaataatac atggcaaatc tagtcccттта tgcagaaatt cattgctggt   2220
ggctccaaga tgcaatataa ttacacctct cttcctgcca gctgtaccac agctagtgcc   2280
ctagtgtatg aaataatccc tctgtctttc accagcactg tggccatccg tctgagagcc   2340
atgaccctgg ctgggagggg acgaagacac cagggaatgg aaaataaaag gaaaagtaca   2400
gaaa                                                                2404
```

<210> SEQ ID NO 2
<211> LENGTH: 328
<212> TYPE: PRT
<213> ORGANISM: homo sapiens

<400> SEQUENCE: 2

```
Met Gly Val Leu Arg Val Gly Leu Cys Pro Gly Leu Thr Glu Glu Met
1               5                   10                  15

Ile Gln Leu Leu Arg Ser His Arg Ile Lys Thr Val Val Asp Leu Val
            20                  25                  30

Ser Ala Asp Leu Glu Glu Val Ala Gln Lys Cys Gly Leu Ser Tyr Lys
        35                  40                  45

Ala Leu Val Ala Leu Arg Arg Val Leu Leu Ala Gln Phe Ser Ala Phe
    50                  55                  60

Pro Val Asn Gly Ala Asp Leu Tyr Glu Glu Leu Lys Thr Ser Thr Ala
65                  70                  75                  80

Ile Leu Ser Thr Gly Ile Gly Ser Leu Asp Lys Leu Leu Asp Ala Gly
                85                  90                  95

Leu Tyr Thr Gly Glu Val Thr Glu Ile Val Gly Gly Pro Gly Ser Gly
            100                 105                 110

Lys Thr Gln Val Cys Leu Cys Met Ala Ala Asn Val Ala His Gly Leu
        115                 120                 125

Gln Gln Asn Val Leu Tyr Val Asp Ser Asn Gly Gly Leu Thr Ala Ser
    130                 135                 140

Arg Leu Leu Gln Leu Leu Gln Ala Lys Thr Gln Asp Glu Glu Glu Gln
145                 150                 155                 160

Ala Glu Ala Leu Arg Arg Ile Gln Val Val His Ala Phe Asp Ile Phe
                165                 170                 175

Gln Met Leu Asp Val Leu Gln Glu Leu Arg Gly Thr Val Ala Gln Gln
            180                 185                 190

Val Thr Gly Ser Ser Gly Thr Val Lys Val Val Val Asp Ser Val
        195                 200                 205

Thr Ala Val Val Ser Pro Leu Leu Gly Gly Gln Gln Arg Glu Gly Leu
    210                 215                 220
```

-continued

```
Ala Leu Met Met Gln Leu Ala Arg Glu Leu Lys Thr Leu Ala Arg Asp
225                 230                 235                 240

Leu Gly Met Ala Val Val Val Thr Asn His Ile Thr Arg Asp Arg Asp
                245                 250                 255

Ser Gly Arg Leu Lys Pro Ala Leu Gly Arg Ser Trp Ser Phe Val Pro
            260                 265                 270

Ser Thr Arg Ile Leu Leu Asp Thr Ile Glu Gly Ala Gly Ala Ser Gly
        275                 280                 285

Gly Arg Arg Met Ala Cys Leu Ala Lys Ser Ser Arg Gln Pro Thr Gly
    290                 295                 300

Phe Gln Glu Met Val Asp Ile Gly Thr Trp Gly Thr Ser Glu Gln Ser
305                 310                 315                 320

Ala Thr Leu Gln Gly Asp Gln Thr
                325

<210> SEQ ID NO 3
<211> LENGTH: 20
<212> TYPE: DNA
<213> ORGANISM: artificial sequence
<220> FEATURE:
<223> OTHER INFORMATION: sequencing primer forward

<400> SEQUENCE: 3
gcctcctcct ctctcctttc                                             20

<210> SEQ ID NO 4
<211> LENGTH: 19
<212> TYPE: DNA
<213> ORGANISM: artificial sequence
<220> FEATURE:
<223> OTHER INFORMATION: Sequencing primer reverse

<400> SEQUENCE: 4
cacccttcct gagcctctc                                              19

<210> SEQ ID NO 5
<211> LENGTH: 21
<212> TYPE: DNA
<213> ORGANISM: artificial sequence
<220> FEATURE:
<223> OTHER INFORMATION: SEQUENCING PRIMER FORWARD

<400> SEQUENCE: 5
gggtagaatt gacaccccat t                                           21

<210> SEQ ID NO 6
<211> LENGTH: 22
<212> TYPE: DNA
<213> ORGANISM: Artificial sequence
<220> FEATURE:
<223> OTHER INFORMATION: SEQUENCING PRIMER REVERSE

<400> SEQUENCE: 6
tgacttctga ctccaagtga cc                                          22

<210> SEQ ID NO 7
<211> LENGTH: 20
<212> TYPE: DNA
<213> ORGANISM: artificial sequence
<220> FEATURE:
<223> OTHER INFORMATION: SEQUENCING PRIMER FORWARD

<400> SEQUENCE: 7
```
aaagggagca gagggttctc                                              20

<210> SEQ ID NO 8
<211> LENGTH: 20
<212> TYPE: DNA
<213> ORGANISM: artificial sequence
<220> FEATURE:
<223> OTHER INFORMATION: SEQUENCING PRIMER REVERSE

<400> SEQUENCE: 8
atgtcctgac cccttctctt                                              20

<210> SEQ ID NO 9
<211> LENGTH: 20
<212> TYPE: DNA
<213> ORGANISM: artificial sequence
<220> FEATURE:
<223> OTHER INFORMATION: sequencing primer forward

<400> SEQUENCE: 9
tggccagtga tgttcaaaga                                              20

<210> SEQ ID NO 10
<211> LENGTH: 21
<212> TYPE: DNA
<213> ORGANISM: artificial sequence
<220> FEATURE:
<223> OTHER INFORMATION: sequencing primer reverse

<400> SEQUENCE: 10
cccattagta cgctgaagct c                                            21

<210> SEQ ID NO 11
<211> LENGTH: 20
<212> TYPE: DNA
<213> ORGANISM: artificial sequence
<220> FEATURE:
<223> OTHER INFORMATION: sequencing primer forward

<400> SEQUENCE: 11
ggactcagcc catttgtgtt                                              20

<210> SEQ ID NO 12
<211> LENGTH: 20
<212> TYPE: DNA
<213> ORGANISM: artificial sequence
<220> FEATURE:
<223> OTHER INFORMATION: sequencing primer reverse

<400> SEQUENCE: 12
agcaagtttg aaggcaagga                                              20

<210> SEQ ID NO 13
<211> LENGTH: 20
<212> TYPE: DNA
<213> ORGANISM: artificial sequence
<220> FEATURE:
<223> OTHER INFORMATION: sequencing primer forward

<400> SEQUENCE: 13
ctgagtcctt gcatccaggt                                              20

<210> SEQ ID NO 14
<211> LENGTH: 20
<212> TYPE: DNA
<213> ORGANISM: artificial sequence

```
<220> FEATURE:
<223> OTHER INFORMATION: sequencing primer reverse

<400> SEQUENCE: 14
attgcacatc tgcatttcca                                              20

<210> SEQ ID NO 15
<211> LENGTH: 20
<212> TYPE: DNA
<213> ORGANISM: artificial sequence
<220> FEATURE:
<223> OTHER INFORMATION: sequencing primer forward

<400> SEQUENCE: 15
cttgctgtat ttgggatggg                                              20

<210> SEQ ID NO 16
<211> LENGTH: 20
<212> TYPE: DNA
<213> ORGANISM: artificial sequence
<220> FEATURE:
<223> OTHER INFORMATION: sequencing primer reverse

<400> SEQUENCE: 16
tttggggttc agaagctgac                                              20

<210> SEQ ID NO 17
<211> LENGTH: 20
<212> TYPE: DNA
<213> ORGANISM: artificial sequence
<220> FEATURE:
<223> OTHER INFORMATION: sequencing primer forward

<400> SEQUENCE: 17
ctctccgtaa aatgaagcgg                                              20

<210> SEQ ID NO 18
<211> LENGTH: 20
<212> TYPE: DNA
<213> ORGANISM: artificial sequence
<220> FEATURE:
<223> OTHER INFORMATION: SEQUENCING PRIMER REVERSE

<400> SEQUENCE: 18
taaacagcag gcgttactgg                                              20

<210> SEQ ID NO 19
<211> LENGTH: 22
<212> TYPE: DNA
<213> ORGANISM: artificial sequence
<220> FEATURE:
<223> OTHER INFORMATION: internal primer for tumor analysis

<400> SEQUENCE: 19
cagaaccagt gcttgaaaga aa                                           22

<210> SEQ ID NO 20
<211> LENGTH: 21
<212> TYPE: DNA
<213> ORGANISM: artificial sequence
<220> FEATURE:
<223> OTHER INFORMATION: internal primer for tumor analysis

<400> SEQUENCE: 20
ggcctcacat gtacctgagt t                                            21
```

```
<210> SEQ ID NO 21
<211> LENGTH: 20
<212> TYPE: DNA
<213> ORGANISM: artificial sequence
<220> FEATURE:
<223> OTHER INFORMATION: internal primer for tumor analysis

<400> SEQUENCE: 21
gaatctgggc aaggtttggt                                            20

<210> SEQ ID NO 22
<211> LENGTH: 20
<212> TYPE: DNA
<213> ORGANISM: artificial sequence
<220> FEATURE:
<223> OTHER INFORMATION: internal primer for tumor analysis

<400> SEQUENCE: 22
tgggttttag cctgaagcag                                            20

<210> SEQ ID NO 23
<211> LENGTH: 20
<212> TYPE: DNA
<213> ORGANISM: artificial sequence
<220> FEATURE:
<223> OTHER INFORMATION: internal primer for tumor analysis

<400> SEQUENCE: 23
aggcctctgt tttcctctcc                                            20

<210> SEQ ID NO 24
<211> LENGTH: 20
<212> TYPE: DNA
<213> ORGANISM: artificial sequence
<220> FEATURE:
<223> OTHER INFORMATION: internal primer for tumor analysis

<400> SEQUENCE: 24
cgatggtgtc caggagaatc                                            20
```